US009962691B2

(12) United States Patent
Ragheb et al.

(10) Patent No.: US 9,962,691 B2
(45) Date of Patent: May 8, 2018

(54) CHROMATOGRAPHY MEMBRANES FORMED BY THIOL-ENE OR THIOL-YNE CLICK POLYMERIZATION REACTIONS

(71) Applicant: Natrix Separations Inc., Burlington (CA)

(72) Inventors: Amro Ragheb, Mississauga (CA); Gary Skarja, Toronto (CA)

(73) Assignee: Natrix Separations Inc., Burlington, Ontario (CA)

( * ) Notice: Subject to any disclaimer, the term of this patent is extended or adjusted under 35 U.S.C. 154(b) by 0 days. days.

(21) Appl. No.: 15/049,625

(22) Filed: Feb. 22, 2016

(65) Prior Publication Data
US 2016/0243538 A1    Aug. 25, 2016

Related U.S. Application Data

(60) Provisional application No. 62/118,577, filed on Feb. 20, 2015.

(51) Int. Cl.
| | | |
|---|---|---|
| *B01J 39/26* | (2006.01) | |
| *B01J 39/18* | (2017.01) | |
| *B01D 15/34* | (2006.01) | |
| *C07K 1/18* | (2006.01) | |
| *C07K 1/22* | (2006.01) | |
| *B01J 39/19* | (2017.01) | |

(52) U.S. Cl.
CPC ............ *B01J 39/185* (2013.01); *B01D 15/34* (2013.01); *B01J 39/19* (2017.01); *B01J 39/26* (2013.01); *C07K 1/18* (2013.01); *C07K 1/22* (2013.01)

(58) Field of Classification Search
USPC ............................................ 521/27; 522/180
See application file for complete search history.

(56) References Cited

U.S. PATENT DOCUMENTS 8,440,736 B2    5/2013    Hoyle et al.

FOREIGN PATENT DOCUMENTS

| CN | 104592526 A | 5/2015 |
| CN | 105694051 A | 6/2016 |
| EP | 2606915 A2 * | 6/2013 |

(Continued)

OTHER PUBLICATIONS

Daniele, et al., "Interpenetrating networks based on gelatin methacrylamide and PEG formed using concurrent thiol click chemistries for hydrogel tissue engineering scaffolds," Biomaterials, 35: 1845-1856 (2014).*

(Continued)

*Primary Examiner* — Mark Kaucher
*Assistant Examiner* — Henry Hu
(74) *Attorney, Agent, or Firm* — Dana M. Gordon; Foley Hoag LLP

(57) ABSTRACT

Disclosed are composite materials and methods of making them. The composite materials comprise a support member and a cross-linked gel, wherein the cross-linked gel is a polymer synthesized by thiol-ene or thiol-yne polymerization and cross-linking. The cross-linked gel may be functionalized by a thiol-ene or thiol-yne grafting reaction, either simultaneously with the polymerization or as the second step in a two-step procedure. The composite materials are useful as chromatographic separation media.

22 Claims, 21 Drawing Sheets

(56) References Cited

FOREIGN PATENT DOCUMENTS

EP          2606915 A2     6/2013

OTHER PUBLICATIONS

Cleophas, et al., "Characterization and Activity of an Immobilized Antimicrobial Peptide Containing Bactericidal PEG-Hydrogel," Biomacromolecules, 15: 3390-3395 (2014).*
Cai et al., "Poly(vinylidene fluoride) Graft Copolymer Membranes with "Clickable" Surfaces and their Functionalization," Macromolecules, 44:4258-4268 (2011).*
Cai, et al., "Functional poly(vinylidene fluoride) copolymer membranes via surface-initiated thiol-ene click reactions," Polym Chem, 2: 1849 (2011).
Carlborg, et al., "Beyond PDMS: off-stoichiometry thiol-ene (OSTE) based soft lithography for rapid prototyping of microfluidic devices," Lab Chip, 11: 3136 (2011).
Kwisnek, et al., "PEG Containing Thiol-Ene Network Membranes for CO2 Separation: Effect of Cross-Linking on Thermal, Mechanical, and Gas Transport Properties," Macromolecules, 47: 3243-3253 (2014).
Liu, et al., "Responsive hybrid microcapsules by the one-step interfacial thiol-ene photopolymerization," Langmuir, 29(17): 5307-5314 (2013).
Lovelady, et al., "Preparation of emulsion-templated porous polymers using thiol-ene and thiol-yne chemistry," Polym Chem, 2: 559-562 (2011).
Lowe, et al., "Thiol-yne 'click'/coupling chemistry and recent applications in polymer and materials synthesis and modification," Polymer, 55: 5517-5549 (2014).
McCall, et al., "Thiol-Ene Photopolymerizations Provide a Facile Method to Encapsulate Proteins and Maintain Their Bioactivity," Biomacromolecules, 13: 2410-2417 (2012).
Jiang et al., "Cross-linked high conductive membranes based on water soluble ionomer for high performance proton exchange membrane fuel cells," Journal of Power Sources, 241:529-535 (2013).
Wang et al., "Surface glycolsylation of polymer membrane by thiol-yne click chemistry for affinity adsorption of lectin," Chemical Communications, 47:3930-3932 (2011).
International Search Report dated Jul. 20, 2016, from PCT/IB2016/000297.
Hoyle et al., "Thiol-Ene click chemistry," Angew Chem Int Edit, 49(9): 1540-1573 (2010).

\* cited by examiner

Figure 1

| Formula | wt.% | | | | | | | | Alkene/thiol ratio | RO Flux (kg/m²h) | Mass Gain wt.% | Wetting Time (s) |
|---|---|---|---|---|---|---|---|---|---|---|---|---|
| | EDDET | TATATO | TEGDV | DMAc | DPMA | 1,3-budiol | DI water | IRGA-CURE | | | | |
| CLK-EN-016 | 15.3 | 14.6 | 5.3 | 25.2 | 18.9 | 15.8 | 4.4 | 0.46 | 1.36 | 2189 | 240 | 40 |
| CLK-EN-012 | 15.3 | 13.3 | 6.6 | 25.2 | 18.9 | 15.8 | 4.4 | 0.46 | 1.35 | 432 | 239 | 40 |
| CLK-EN-017 | 15.3 | 13.3 | 6.6 | 25.3 | 16.6 | 18.0 | 4.5 | 0.47 | 1.35 | 2119 | 236 | 40 |
| CLK-EN-040 | 15.3 | 13.3 | 7.3 | 23.9 | 16.6 | 18.6 | 4.5 | 0.47 | 1.39 | 4002 | 248 | 15 |
| CLK-EN-090 | 15.8 | 6.3 | 11.5 | 26.4 | 19.8 | 16.5 | 3.3 | 0.33 | 1.10 | 931 | 219 | 110 |
| CLK-EN-081 | 15.8 | 6.3 | 11.5 | 26.4 | 13.2 | 23.1 | 3.3 | 0.33 | 1.10 | 7307 | 230 | 25 |
| CLK-EN-083 | 15.9 | 7.3 | 10.3 | 26.5 | 16.6 | 19.9 | 3.3 | 0.33 | 1.08 | 1154 | 231 | >120 |
| CLK-EN-084 | 15.9 | 7.3 | 10.3 | 26.5 | 23.2 | 13.2 | 3.3 | 0.33 | 1.08 | 711 | 223 | 60 |
| CLK-EN-092 | 16.6 | 5.3 | 13.3 | 23.3 | 21.3 | 17.9 | 2.0 | 0.33 | 1.07 | 1116 | 231 | 25 |
| CLK-EN-108 | 16.6 | 5.3 | 13.3 | 23.3 | 20.6 | 18.6 | 2.0 | 0.33 | 1.07 | 1296 | 231 | 20 |

Figure 2

| Formula | wt.% | | | | | | | Alkene/thiol ratio | RO Flux (kg/m²h) | Mass Gain wt.% | Wetting Time (s) |
|---|---|---|---|---|---|---|---|---|---|---|---|
| | EDDET | TATATO | TEGDV | DMAc | DPMA | 1,3-budiol | DI water | IRGA-CURE | | | | |
| CLK-EN-045 10 min | 16.6 | 13.3 | 6.7 | 24.0 | 17.3 | 20.0 | 2.0 | 0.20 | 1.24 | 3753 | 238 | 16 |
| CLK-EN-027 10 min | 16.6 | 13.3 | 6.6 | 23.9 | 17.3 | 19.9 | 2.0 | 0.46 | 1.24 | 1468 | 243 | 10 |
| CLK-EN-137 6 min | 16.2 | 12.3 | 7.4 | 27.0 | 13.5 | 20.2 | 3.4 | 0.07 | 1.25 | 6435 | 241 | 50 |
| CLK-EN-138 6 min | 16.2 | 12.3 | 7.4 | 26.9 | 13.5 | 20.2 | 3.4 | 0.20 | 1.25 | 4499 | 247 | 15 |
| CLK-EN-139 6 min | 16.1 | 12.3 | 7.4 | 26.9 | 13.4 | 20.1 | 3.4 | 0.47 | 1.25 | 3858 | 246 | 20 |
| CLK-EN-140 6 min | 16.1 | 12.2 | 7.4 | 26.8 | 13.4 | 20.1 | 3.4 | 0.67 | 1.25 | 3392 | 242 | 15 |

Figure 3

| Formula | wt.% | | | | | | | | | Alkene/thiol ratio | RO Flux (kg/m²h) | Mass Gain wt.% | Wetting Time (s) |
|---|---|---|---|---|---|---|---|---|---|---|---|---|---|
| | EDDET | TATATO | TEGDV | DATA | DMAc | DPMA | 1,3-budiol | DI water | IRGA-CURE | | | | |
| CLK-EN-099 | 15.8 | 7.9 | 7.9 | 3.3 | 26.4 | 15.2 | 19.8 | 3.3 | 0.33 | 1.17 | 10091 | 232 | 6 |
| CLK-EN-104 | 15.8 | 7.9 | 7.9 | 3.3 | 27.7 | 15.2 | 18.5 | 3.3 | 0.33 | 1.17 | 1696 | 235 | 15 |
| CLK-EN-105 | 15.8 | 7.9 | 7.9 | 3.3 | 26.4 | 17.8 | 18.5 | 2.0 | 0.33 | 1.17 | 1537 | 230 | 15 |
| CLK-EN-106 | 15.9 | 7.9 | 7.9 | 3.3 | 27.8 | 16.6 | 17.9 | 2.3 | 0.33 | 1.17 | 930 | 230 | 15 |

Figure 4A

| Formula | wt.% | | | | | | | | Alkene/thiol ratio | RO Flux (kg/m²h) | Mass Gain wt.% | Wetting Time (s) |
|---|---|---|---|---|---|---|---|---|---|---|---|---|
| | EDDET | TATATO | DATA | DMAc | DPMA | 1,3-Budiol | DI water | IRGA-CURE | | | | |
| CLK-EN-118 | 14.6 | 14.6 | 3.3 | 25.2 | 17.3 | 19.9 | 4.8 | 0.27 | 1.28 | 11509 | 223 | 15 |
| CLK-EN-124 | 16.3 | 16.5 | 3.3 | 24.6 | 16.6 | 18.6 | 4.0 | 0.27 | 1.27 | 14895 | 241 | 10 |
| CLK-EN-143 | 17.3 | 9.8 | 7.5 | 32.1 | 12.0 | 14.2 | 7.1 | 0.17 | 0.963 | 9007 | 272 | 1 |
| CLK-EN-149 | 17.4 | 9.8 | 7.5 | 32.3 | 12.0 | 13.6 | 7.1 | 0.20 | 0.96 | 3804 | 253 | 1 |
| CLK-EN-150 | 16.7 | 9.9 | 7.5 | 32.7 | 12.1 | 13.7 | 7.1 | 0.20 | 1.01 | 6700 | 245 | 1 |
| CLK-EN-151 | 16.2 | 9.9 | 7.6 | 33.0 | 12.2 | 13.7 | 7.2 | 0.20 | 1.05 | 7808 | 237 | 1 |
| CLK-EN-152 | 18.0 | 10.1 | 7.8 | 32.0 | 11.4 | 12.9 | 7.5 | 0.20 | 0.963 | 7674 | 260.3 | 1 |

Figure 4B

| Formula | wt.% | | | | | | | | Alkene/thiol ratio | RO Flux (kg/m²h) | Mass Gain wt.% | Wetting Time (s) |
|---|---|---|---|---|---|---|---|---|---|---|---|---|
| | EDDET | TATATO | DATA | DMAc | DPMA | 1,3-Budiol | DI water | IRGA-CURE | | | | |
| CLK-EN-276 | 17.25 | 11.94 | 8.29 | 36.48 | 13.27 | 5.97 | 6.63 | 0.17 | 1.143 | 1254 | 243 | 10 |

Figure 7

| Formula | wt.% | | | | | | | | | | Alkene/thiol ratio | RO Flux (kg/m²h) | Mass Gain wt.% | Wetting Time (s) |
| --- | --- | --- | --- | --- | --- | --- | --- | --- | --- | --- | --- | --- | --- | --- |
| | EDDET | OctDi | TATATO | TEGDV | DATA | DMAc | DPMA | 1,3-Budiol | DI water | IRGA-CURE | | | | |
| CLK-EN-049 | 16.7 | 3.1 | 18.5 | 1.5 | | 22.2 | 16.7 | 16.7 | 4.3 | 0.31 | 1.94 | 7257 | 306 | >120 |
| CLK-EN-052 | 16.3 | 1.6 | 16.3 | 3.3 | | 24.7 | 16.9 | 16.3 | 4.4 | 0.33 | 1.62 | 3672 | 273 | >120 |
| CLK-EN-120 | 15.8 | 1.1 | 8.1 | | 7.4 | 35.4 | 12.9 | 12.9 | 6.1 | 0.29 | 1.18 | 142 | 223 | 60 |
| CLK-EN-134 | 17.3 | 1.3 | 9.0 | | 5.5 | 33.2 | 12.0 | 16.6 | 5.0 | 0.30 | 1.074 | 6979 | 236 | 2 |

Figure 9

| Formula | wt.% | | | | | | | | | | Alkene/thiol ratio | RO Flux | Mass Gain wt% | Wetting Time (s) |
|---|---|---|---|---|---|---|---|---|---|---|---|---|---|---|
| | EDDET | OctDi | TATATO | TEGDV | DATA | DMAc | DPMA | 1,3-budiol | DI water | IRGA-CURE | | | | |
| CLK-EN-015 | 13.8 | | 12.0 | 6.0 | | 26.6 | 19.9 | 16.6 | 4.7 | 0.47 | 1.35 | 21917 | 214.7 | 40 |
| CLK-EN-042 | 15.3 | | 14.6 | 6.7 | | 32.6 | | 28.3 | 2.0 | 0.47 | 1.44 | 27143 | 235.5 | 6 |
| CLK-EN-046 | 15.3 | | 14.6 | 6.6 | | 30.5 | | 29.4 | 3.3 | 0.33 | 1.44 | 23509 | 235.8 | 2 |
| CLK-EN-112 | 14.1 | | 11.4 | | 6.0 | 32.9 | 13.4 | 15.4 | 6.4 | 0.27 | 1.23 | 15758 | 208.6 | 1 |
| CLK-EN-113 | 14.6 | | 11.3 | | 6.6 | 32.6 | 13.3 | 15.3 | 6.0 | 0.27 | 1.21 | 13612 | 223.4 | 1 |
| CLK-EN-133 | 17.4 | 1.3 | 9.1 | | 5.5 | 33.4 | 13.4 | 13.4 | 6.3 | 0.30 | 1.08 | 15531 | 229.3 | 1 |

Figure 12

| Experiment | Final Coupling Buffer | Additive | Reaction Volume (mL) | Ligand Conc. (mg/mL) | Total ligand amount (mg) | Exposure time (min) | Binding Capacity (mg/mL) | Initiator amount (mg) |
|---|---|---|---|---|---|---|---|---|
| EN-143A | 250 mM phosphate buffer, pH 7.2 | None | 0.5 | 25 | 12.5 | 10 | 4.9 | 1.9 |
| EN-143B | 225 mM phosphate buffer, pH 7.2 | 50 μL of cysteamine-HCl | 0.55 | 22.8 | 12.5 | 10 | 0.5 | 1.9 |
| EN-143C | 225 mM phosphate buffer, pH 7.2 | 50 μL of 1-mercapto-ethanol | 0.55 | 22.8 | 12.5 | 10 | 0.5 | 1.9 |

Figure 13

| Formula | EDDET | TATATO | DATA | DMAc | Hexylene glycol | 1,3-Budiol | Tet EG | TEG | DI water | IRGA-CURE | Total | Alkene/thiol ratio | RO Flux (kg/m²h) | Mass Gain wt. % | Wetting Time (s) |
|---|---|---|---|---|---|---|---|---|---|---|---|---|---|---|---|
| | | | | | wt. % | | | | | | | | | | |
| CLK-EN-224 | 15.60 | 9.43 | 9.10 | 39.01 | - | 18.21 | - | - | 8.45 | 0.20 | 100 | 1.129 | 17189 | 238 | 1 |
| CLK-EN-237 | 16.96 | 10.85 | 8.48 | 37.17 | - | 18.85 | - | - | 7.50 | 0.20 | 100 | 1.101 | 15432 | 258 | 1 |
| CLK-EN-235 | 17.34 | 11.74 | 8.67 | 40.03 | - | 11.34 | - | 3.34 | 7.34 | 0.20 | 100 | 1.142 | 12243 | 262 | 1 |
| CLK-EN-256 | 17.04 | 12.78 | 8.52 | 38.01 | - | 13.11 | - | 4.59 | 5.90 | 0.07 | 100 | 1.222 | 16246 | 261 | 1 |
| CLK-EN-227 | 16.95 | 10.84 | 8.47 | 38.13 | - | 13.69 | - | 4.56 | 7.17 | 0.20 | 100 | 1.101 | 13664 | 259 | 1 |
| CLK-EN-287 | 17.12 | 11.20 | 8.96 | 38.20 | - | 3.29 | 13.17 | 0.00 | 7.90 | 0.16 | 100 | 1.135 | 6972 | 267 | 1 |
| CLK-EN-291 | 17.09 | 11.83 | 8.54 | 36.15 | 11.83 | 6.57 | - | 0.00 | 7.89 | 0.10 | 100 | 1.159 | 10172 | 264 | 1 |
| CLK-EN-298 | 17.03 | 11.79 | 8.52 | 36.03 | 11.14 | - | 6.55 | 0.00 | 8.84 | 0.10 | 100 | 1.159 | 6918 | 249 | 1 |
| CLK-EN-301 | 16.51 | 12.22 | 8.26 | 35.67 | 15.85 | 2.41 | - | 0.00 | 8.92 | 0.17 | 100 | 1.211 | 13841 | 243 | 1 |

Figure 15

| Formula | wt. % | | | | | | | | | | Alkene/thiol ratio | RO Flux (kg/m²h) | Mass Gain wt. % | Wetting Time |
|---|---|---|---|---|---|---|---|---|---|---|---|---|---|---|
| | EDDET | PETM | TATATO | DATA | DMAc | Hexylene glycol | 1,3-Budiol | TetEG | EG | DI water | IRGACURE | | | | |
| CLK-EN-314 | 15.01 | 2.28 | 10.77 | 8.81 | 37.85 | - | 3.92 | 13.05 | - | 8.16 | 0.16 | 1.128 | 6781 | 253 | 1 sec |
| CLK-EN-317 | 14.85 | 2.22 | 11.75 | 8.16 | 36.89 | 9.79 | 9.14 | 0 | - | 7.02 | 0.16 | 1.176 | 7995 | 242 | 1 sec |
| CLK-EN-323 | 13.94 | 3.98 | 11.95 | 8.63 | 38.83 | - | 4.65 | 8.63 | - | 9.29 | 0.10 | 1.183 | 14788 | 247 | 1 sec |
| CLK-EN-325 | 13.36 | 3.84 | 11.52 | 8.02 | 36.74 | 9.35 | 6.68 | 0 | 3.34 | 7.01 | 0.13 | 1.174 | 11812 | 241 | 1 sec |

Figure 17

| Formula | wt. % | | | | | | | | | Alkene/thiol ratio | RO Flux (kg/m²h) | Mass Gain wt.% | Wetting Time |
|---|---|---|---|---|---|---|---|---|---|---|---|---|---|
| | EDDET | OctDi | TAT ATO | DATA | DMAc | SDS | Tet EG | EG | DI water | IRGA-CURE | | | | |
| CLK-EN-361 | 16.34 | 2.14 | 5.03 | 11.62 | 42.10 | 1.57 | 4.71 | 5.03 | 11.31 | 0.16 | 1.355 | 2769 | 222 | 2 sec |
| CLK-EN-365 | 16.54 | 2.16 | 5.09 | 11.14 | 41.36 | 0.00 | 6.36 | 6.36 | 10.82 | 0.16 | 1.324 | 22176 | 243 | 1 sec |

| Formula | wt. % | | | | | | | | | | | | Alkene/thiol ratio | Mass Gain wt.% | Wetting Time |
|---|---|---|---|---|---|---|---|---|---|---|---|---|---|---|---|
| | EDDET | OctSH | DTT | OctDi | TATATO | DATA | DMAc | SDS | TetEG | EG | DI water | IRGA-CURE | | | |
| CLK-EN-411 | 17.53 | 0.94 | 0.63 | 2.19 | 6.89 | 10.33 | 42.25 | 1.56 | 3.13 | 5.01 | 9.39 | 0.16 | 1.237 | 246 | 2 sec |
| CLK-EN-417 | 17.15 | 1.53 | 0.92 | 0.00 | 11.94 | 10.11 | 41.35 | 1.53 | 3.06 | 3.06 | 9.19 | 0.15 | 1.093 | 265 | 2 sec |

Figure 21

| Formula | Wt.% | | | | | | Alkene/thiol ratio | RO Flux (kg/m²h) | Mass Gain wt% | Wetting Time |
|---|---|---|---|---|---|---|---|---|---|---|
| | EDDET | TATATO | DATA | DMAc | 1,3-Budiol | DI water | IRGA-CURE | | | | |
| CLK-EN-224-DP-A | 6.16 | 4.46 | 4.66 | 58.31 | 14.58 | 11.66 | 0.17 | 1.398 | 2238 | 309 | 1 Sec |
| CLK-EN-224-DP-B | 6.26 | 5.67 | 3.13 | 58.41 | 14.69 | 11.68 | 0.17 | 1.394 | 984 | 311 | 1 Sec |
| CLK-EN-224-DP-C | 6.34 | 2.92 | 5.84 | 58.43 | 14.61 | 11.69 | 0.17 | 1.241 | 1706 | 300 | 1 Sec |
| CLK-EN-224-DP-D | 7.02 | 4.15 | 3.95 | 50.66 | 22.43 | 11.63 | 0.17 | 1.098 | 6832 | 311 | 1 Sec |

Figure 22

| Formula | Mass Gain Increase (wt.%) due to 2nd polym. | Polymn. Mass % | Alkene/thiol ratio | RO Flux (kg/m²h) | Bioaffinity IgG Binding Capacity$_{10\%B.T}$ (mg/mL) | CEX gG Binding Capacity$_{10\%B.T}$ (mg/mL) | mole % | | |
|---|---|---|---|---|---|---|---|---|---|
| | | | | | | | EDDET | TATATO | DATA |
| CLK-EN-224 (Base) | - | 34.14 | 1.129 | 17189 | 6.0 | 28.1 | 52.1 | 23.0 | 24.9 |
| CLK-EN-224-DP-A | 71 | 15.29 | 1.398 | 2238 | 5.1 | 15.9 | 46.4 | 24.5 | 28.0 |
| CLK-EN-224-DP-B | 73 | 15.06 | 1.394 | 984 | 4.6 | 9.3 | 48.0 | 31.8 | 19.2 |
| CLK-EN-224-DP-C | 62 | 15.11 | 1.241 | 1706 | 3.6 | 17.7 | 47.8 | 16.1 | 35.1 |
| CLK-EN-224-DP-D | 73 | 15.12 | 1.098 | 6832 | 7.9 | 16.3 | 52.6 | 22.8 | 23.6 |

CHROMATOGRAPHY MEMBRANES FORMED BY THIOL-ENE OR THIOL-YNE CLICK POLYMERIZATION REACTIONS

RELATED APPLICATIONS

This application claims the benefit of priority to U.S. Provisional Patent Application Ser. No. 62/118,577, filed Feb. 20, 2015, the contents of which are hereby incorporated by reference.

BACKGROUND

"Click chemistry" is the class of reactions that resemble natural, biochemical reactions, with the following attributes: highly efficient, "spring-loaded" reactions that proceed rapidly to high yield; highly selective reactions that produce no (or few) side products and are tolerant of multiple functional groups; and reactions that proceed under mild reaction conditions, such as at low temperatures (e.g., ambient) or in aqueous solutions.

Click chemistry has grown to encompass a range of chemical reactions, such as Diels-Alder reactions, copper-catalyzed alkene-azide cycloaddition (CuAAC), thiol-maleimide addition reactions, and thiol-alkene and thiol-alkyne addition reactions.

The term "thiol-ene" is generally used to describe the hydrothiolation addition of a thiol to any of a wide variety of unsaturated functional groups, such as maleimides, acrylates, and norbornenes, in addition to unactivated carbon-carbon double bonds. In some cases, the reaction can take place not only via the classical radical addition mechanism, but also with Michael-type nucleophilic addition. The term "thiol-yne" is used to describe counterpart hydrothiolation methods using an alkyne in place of an alkene. In general, the thiol-ene and thiol-yne reactions are conducted under photo-initiated radical conditions and proceed via a typical chain growth process with initiation, propagation, and termination steps.

The thiol-ene and -yne click reactions have many attractive features for polymer synthesis. The reactions are rapid, stereo-specific, insensitive to water, and can provide a variety of polymer functionalities through the use of various thiol and/or alkene/alkyne functionalized monomers. By using di-, tri-, and tetra-functionalized thiol and alkene/alkyne monomers, it is possible to perform thiol-ene and -yne click reactions to build new materials with a variety of chemical functionalities. These reactions may also result in more highly organized polymeric networks, in comparison to similar acrylate polymers.

There exists a need for separation or chromatography media that can be easily made by fast, efficient, and easily-controllable polymerization reactions, and easily modified. These media must also display high selectivity and high flow velocity, low back pressure, be inexpensive, and allow for long column-lifetimes, short process-times, and overall operational flexibility.

SUMMARY

In certain embodiments, the invention relates to a composite material, comprising:
a support member, comprising a plurality of pores extending through the support member; and
a cross-linked gel, wherein the cross-linked gel comprises a polymer derived from a first monomer and a first cross-linker;
wherein
the cross-linked gel is located in the pores of the support member;
the first monomer comprises two thiol functional groups; and
the first cross-linker comprises (i) at least three carbon-carbon double bonds, (ii) at least two carbon-carbon triple bonds, or (iii) at least one carbon-carbon triple bond and at least one carbon-carbon double bond.

In certain embodiments, the invention relates to a composite material, comprising:
a support member, comprising a plurality of pores extending through the support member; and
a cross-linked gel, wherein the cross-linked gel comprises a polymer derived from a first monomer, a second monomer, and a first cross-linker;
wherein
the cross-linked gel is located in the pores of the support member;
the first monomer comprises two thiol functional groups;
the second monomer comprises two carbon-carbon double bonds; and
the first cross-linker comprises (i) at least three thiol functional groups, (ii) at least three carbon-carbon double bonds, (iii) at least two carbon-carbon triple bonds, or (iv) at least one carbon-carbon triple bond and at least one carbon-carbon double bond.

In certain embodiments, the invention relates to a method of making a composite material, comprising the steps of:
combining a first monomer a first cross-linker, a photoinitiator, and a solvent, wherein the first monomer comprises two thiol functional groups; and the first cross-linker comprises (i) at least three carbon-carbon double bonds, (ii) at least two carbon-carbon triple bonds, or (iii) at least one carbon-carbon triple bond and at least one carbon-carbon double bond, thereby forming a monomeric mixture;
contacting a support member with the monomeric mixture, thereby forming a modified support member; wherein the support member comprises a plurality of pores extending through the support member, and the average pore diameter of the pores is about 0.1 to about 25 μm;
covering the modified support member with a polymeric sheet, thereby forming a covered support member; and
irradiating the covered support member for a period of time, thereby forming a composite material.

In certain embodiments, the invention relates to a method of making a composite material, comprising the steps of:
combining a first monomer, a second monomer, a first cross-linker, a photoinitiator, and a solvent, wherein the first monomer comprises two thiol functional groups; the second monomer comprises two carbon-carbon double bonds; and the first cross-linker comprises (i) at least three thiol functional groups, (ii) at least three carbon-carbon double bonds, (iii) at least two carbon-carbon triple bonds, or (iv) at least one carbon-carbon triple bond and at least one carbon-carbon double bond, thereby forming a monomeric mixture;
contacting a support member with the monomeric mixture, thereby forming a modified support member; wherein the support member comprises a plurality of pores extending through the support member, and the average pore diameter of the pores is about 0.1 to about 25 μm;
covering the modified support member with a polymeric sheet, thereby forming a covered support member; and
irradiating the covered support member for a period of time, thereby forming a composite material.

In certain embodiments, the invention relates to any one of the aforementioned methods, wherein the monomeric mixture further comprises a plurality of end-group precursors; and the end-group precursors are molecules having a thiol functional group or molecules having an unsaturated carbon-carbon bond.

In certain embodiments, the invention relates to any one of the aforementioned methods, further comprising the steps of:

contacting the composite material with a mixture comprising a photoinitiator and a plurality of end-group precursors, wherein the end-group precursors are molecules having a thiol functional group or molecules having an unsaturated carbon-carbon bond, thereby forming a grafting mixture; and irradiating the grafting mixture for a period of time, thereby forming a modified composite material.

In certain embodiments, the invention relates to a method, comprising the step of:

contacting at a first flow rate a first fluid comprising a substance with any of the composite materials described herein, thereby adsorbing or absorbing a portion of the substance onto the composite material.

BRIEF DESCRIPTION OF THE FIGURES

FIG. 1 tabulates the reaction components (wt. %) and solvents (wt. %) used in the preparation of membranes formed by click alkene reactions using TEGDV as a co-monomer.

FIG. 2 tabulates the reaction components (wt. %) and solvents (wt. %) used in the preparation of membranes formed by click alkene reactions with TEGDV as a co-monomer and varying amounts of initiator.

FIG. 3 tabulates the reaction components (wt. %) and solvents (wt. %) used in the preparation of membranes formed by click alkene reactions with TEGDV and DATA as co-monomers.

FIG. 4A tabulates the reaction components (wt. %) and solvents (wt. %) used in the preparation of membranes formed by click alkene reactions with DATA as a co-monomer.

FIG. 4B tabulates the reaction components (wt. %) and solvents (wt. %) used in the preparation of membranes formed by click alkene reactions with DATA as a co-monomer, at a higher concentration relative to the experiment that is the subject of FIG. 4A.

FIG. 7 tabulates the reaction components (wt. %) and solvents (wt. %) for membranes formed by click alkene reactions with octadiyne as an additional crosslinker.

FIG. 9 tabulates the reaction components (wt. %) and solvents (wt. %) used in the preparation of membranes formed by click alkene reactions and grafted with carboxylate moieties via a second click reaction after polymerization.

FIG. 12 tabulates the binding capacity of three membranes modified with protein A in the absence of thiol-functionalized additives (A), and in the presence of thiol-functionalized additives (B and C).

FIG. 13 tabulates the reaction components (wt. %) and solvents (wt. %) used in the preparation of membranes formed by click alkene reactions with DATA as a co-monomer and a solvent system comprising, for example, triethylene glycol or tetraethylene glycol.

FIG. 15 tabulates the reaction components (wt. %) and solvents (wt. %) used in the preparation of membranes formed by click alkene reactions with PETM as a co-crosslinker.

FIG. 17 tabulates the reaction components (wt. %) and solvents (wt. %) used in the preparation of membranes formed by click alkene reactions with octadiyne as a co-crosslinker.

FIG. 21 tabulates the reaction components (wt. %) and solvents (wt. %) used in a double polymerization reaction.

FIG. 22 tabulates the reaction components (mol. %) used in a double polymerization reaction, and the properties of the resulting membranes.

DETAILED DESCRIPTION

Overview

Figure 5A:
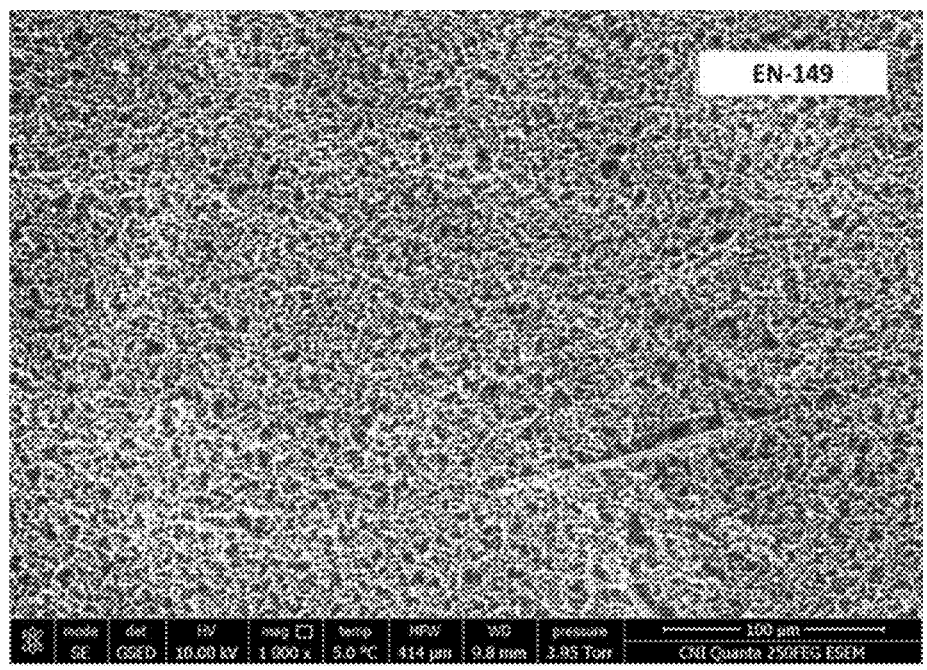
FIG. 5A depicts an ESEM image of a composite membrane formulated with DATA as co-monomer formulated with an alkene-to-thiol ratio (calculated by number of reactive functional groups present, where one alkyne is equivalent to two alkenes because each alkyne may react with two thiols) of 0.96 (EN-149).
Figure 5B:
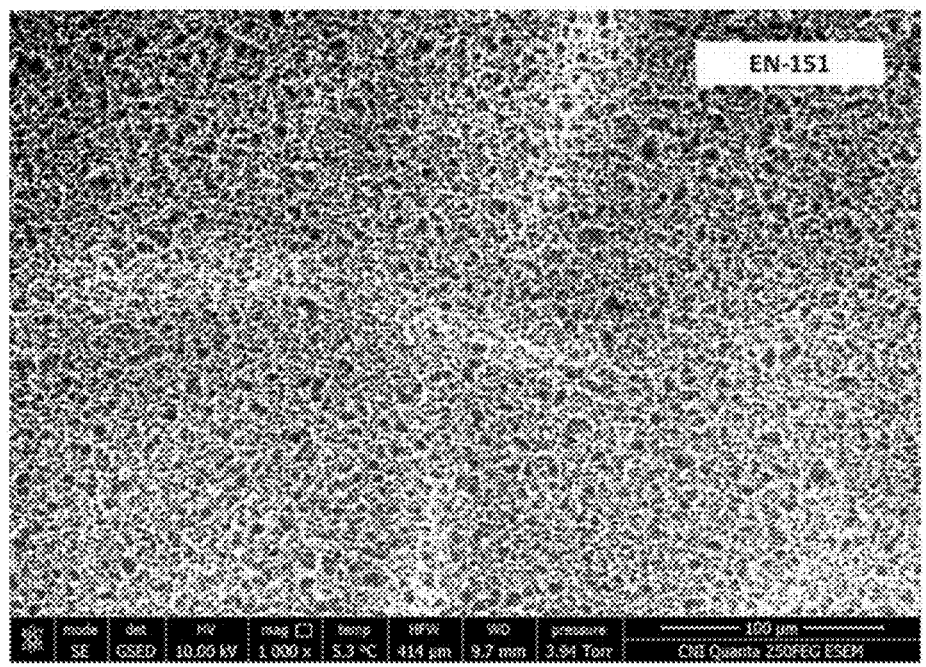
FIG. 5B depicts an ESEM image of a composite membrane formulated with DATA as co-monomer formulated with an alkene-to-thiol ratio (calculated by number of reactive functional groups present, where one alkyne is equivalent to two alkenes because each alkyne may react with two thiols) of 1.05 (EN-151).

While recent work has focused on using thiol-ene and -yne click chemistry to produce various functionalized polymer networks, primarily for film, coating, and dendrimer applications, the approach has not been applied to the production of macroporous network polymer membranes useful for liquid separation processes. In certain embodiments, the invention relates to the use of thiol-ene and -yne click chemistry for the generation of cross-linked polymer membranes suitable for liquid chromatography applications. In certain embodiments, the cross-linked membranes are further grafted with chemical functional groups or molecular species. In certain embodiments, generation of the cross-linked membrane by polymerization, and modification of the cross-linked membrane by grafting, are carried out via highly efficient thiol-ene and/or -yne click reactions (in a one- or two-step procedure).

In certain embodiments, thiol-ene and -yne click chemistry is employed to make a cross-linked polymer that is supported by a fibrous substrate, thereby forming a composite membrane. In certain embodiments, the cross-linked polymers in the composite membranes contain residual reactive groups, such as thiols or unsaturated carbon-carbon bonds, that may be used to attach various chemical compounds or molecular species via additional click reactions.

In certain embodiments, the cross-linked polymer is macroporous. Porosity within the polymers may be promoted during polymerization by degree of crosslinking, solvent exclusion of the polymeric chain during the formation of the polymer network, or some combination of both.

The degree of crosslinking in the polymer may be tuned by adjusting the monomer ratio. Specifically, the alkene-to-thiol ratio is considered to ensure adequate porosity. The chain length of the polymers in the polymeric network and, therefore, the degree of crosslinking may also be controlled by using specific monomers that impart specific physico-chemical properties to the final polymer and membrane. These "tuning" monomers can affect the interaction of the polymer chain with the solvent system. Moreover, the hydrophilicity/hydrophobicity of these monomers can affect the final aqueous swelling properties of the resultant gel and the hydrophilic/hydrophobic surface properties of the polymer network.

Controlling the porosity of the polymer network requires care when using click chemistry because the thiol-ene reaction is so fast. As a result, the movement of the growing chain may be restricted from forming pores. To minimize this undesirable result, the solvent system and monomer are selected to ensure an adequate driving force exists to exclude the growing polymer chains from solution at a certain point, thereby forming macropores. Specifically, the mixture of solvents and non-solvents is tuned to provide a suitable reaction system that can initially dissolve all of reactants but serves as a poor solvent for the cross-linked polymer chains as they grow to be larger than a certain molecular weight. A solvent system with too high a proportion of poor solvent (for the polymer chains) can lead to a rapid precipitation of growing polymer chains, which decreases porosity.

In general, many highly porous and non-rigid polymeric materials are relatively weak and are unable to withstand the pressures generated during typical membrane separation processes (e.g., liquid chromatography). Therefore, in order to make membranes that are mechanically suitable, in certain embodiments a composite material comprising both a porous substrate (such as a woven substrate made of the chemically inert polypropylene) and a porous cross-linked polymer is produced by synthesizing the polymer directly within the substrate pores.

In certain embodiments, when examined using environmental scanning electron microscopy (ESEM), the composite materials showed a well-connected gel network that is incorporated within the substrate fibres.

In certain embodiments, the composite materials of the invention can be effectively used in both "bind-elute" and "flow-through" modes.

"Bind-elute mode" as used herein, refers to an operational approach to chromatography in which the buffer conditions are established so that both a target protein and undesired contaminants bind to the chromatographic support or composite material. Fractionation of target protein from the other components is achieved subsequently by changing the conditions such that the target protein and contaminants are eluted separately. In certain embodiments, the membranes described herein may be used in "bind-elute mode" featuring high dynamic binding capacities at high conductivity, high volume throughput and selectivity. In certain embodiments, the amount of the target protein in the eluent is reduced by about 50% to about 99%. In certain embodiments, the eluent is reduced in aggregates of the target protein by about 90%, about 91%, about 92%, about 93%, about 94%, about 95%, about 96%, about 97%, about 98%, or about 99%.

As used herein, the term "flow-through mode" refers to an operational approach to chromatography in which the buffer conditions are established so that the intact target protein flows through the membrane upon application while contaminants are selectively retained. In certain embodiments, the membranes described herein may be used in "flow-through mode" in a post-protein A purification process to remove key contaminants, such as DNA, host cell proteins (HCP), leached protein A, undesirable aggregates, and viruses in a single step.

Various Characteristics of Exemplary Composite Materials
Composition of the Gels In certain embodiment, the cross-linked polymers may be formed by the reaction between a dithiol monomer and a tri-vinyl monomer or alkyne monomer, which serve as crosslinkers. See Scheme 1A and Scheme 1B. In certain embodiments, additional monomers may be added to tune the final chemical, physical, and mechanical properties of the polymer. In certain embodiments, the cross-linked polymers may be formed by the reaction between a diene monomer and a tri-thiol monomer, which serves as a cross-linker.

Scheme 1A-
Polymer networks produced by thiol-ene click reaction
containing surplus "clickable" functional groups (alkene).

Dithiol
+
Tri-arm alkene

Click rxn
⟶
Excess alkene

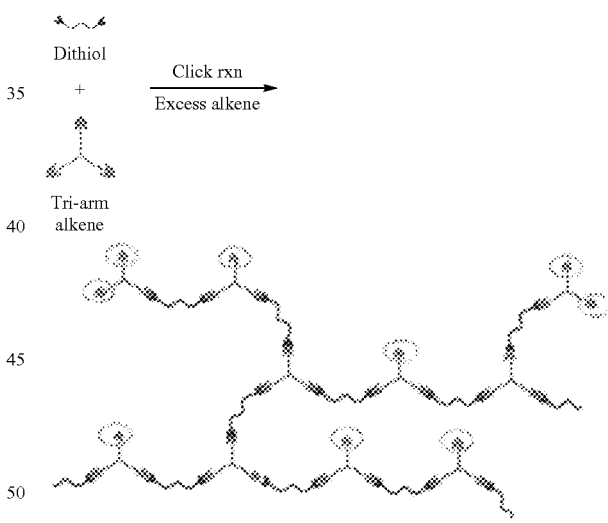

Scheme 1B-
Polymer networks produced by thiol-ene click reaction
containing surplus "clickable" functional groups (thiol).

Dithiol
+
Tri-arm alkene

Click rxn
⟶
Excess Dithiol

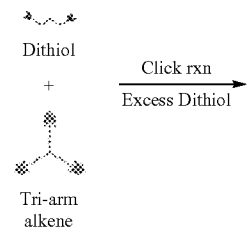

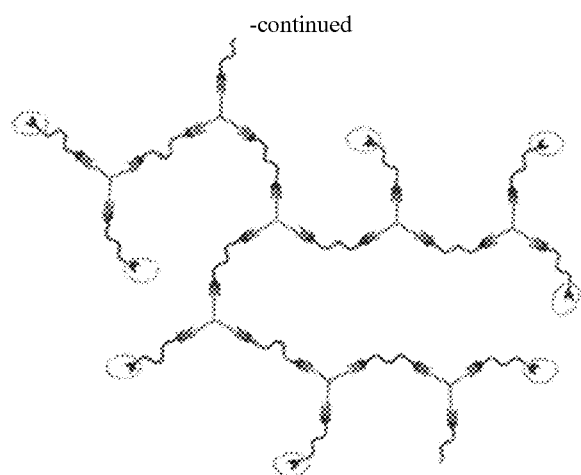

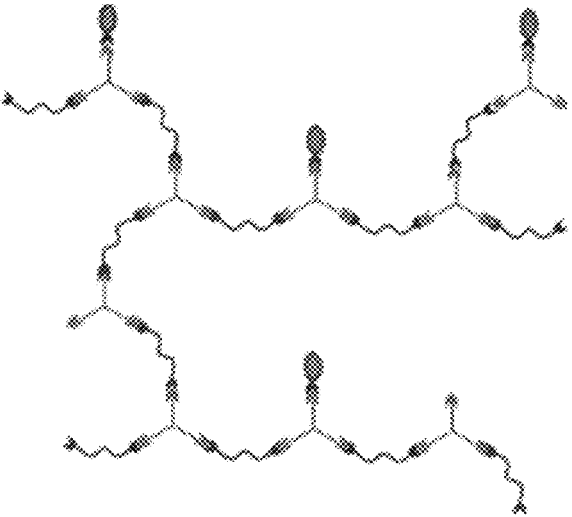

In certain embodiments, the cross-linked polymers may be further functionalized by grafting the cross-linked chains with a grafting moiety. In certain embodiments, the grafting moiety is a thiol or an alkene that also has additional chemical functionalities. In certain embodiments, the cross-linked polymer is formed and grafted in a single step ("one pot" approach, Scheme 2). For example, the inclusion of mercaptosuccininc acid in the polymerization mixture will result in a polymer with carboxylic acid functionality. The inclusion of cysteamine (or alternatively allyl amine) will result in polymer with amine functionality. The use of mercaptoethanesulfonic acid (or alternatively sodium allylsulfonate) will incorporate sulfonic acid groups and negative charges to the polymer network.

Scheme 2-
One pot reaction scheme using thiol-ene click chemistry to produce the polymer network and the grafted functional groups or molecules

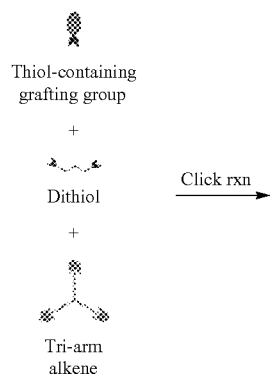

In certain embodiments, the cross-linked polymer may be functionalized by post-polymerization modification. In this two-step method, the excess thiol or alkene groups generated during the thiol-alkene polymerization are modified during a separate grafting step (Scheme 3). By controlling the thiol-to-alkene monomer feed ratio, the final polymers can have a surplus of either alkene or thiol groups. Either functional group can be used subsequently in a grafting reaction, such as a click reaction, to further modify the final polymer chemistry or functionality. In certain embodiments, this approach is useful in making polymeric membranes that contain various ligands useful for chromatographic separation of biomolecules (e.g., proteins). For example, this approach can be used to introduce to the membrane ion exchange functionalities (carboxylate, sulfonate, quaternary ammonium, amine), hydrophobic interaction moieties (such as octyl group by using 1-octanethiol or 1-octene), and biomolecules for bio-affinity chromatography (such as cysteine-protein A for monoclonal antibody purification).

Scheme 3-
Two-step production method to produce grafted thiol-ene click polymers

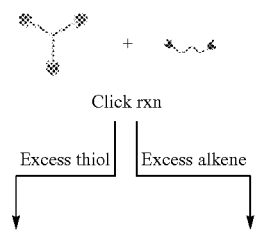

-continued

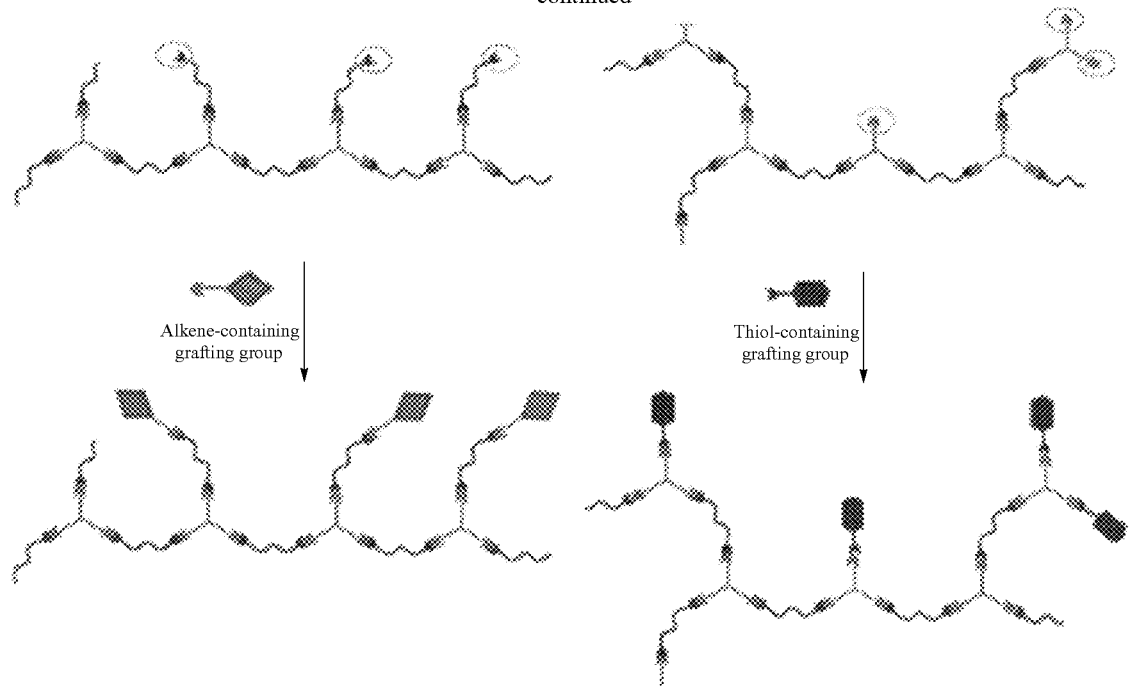

In certain embodiments, thiol-ene grafting is an attractive option for attaching biomolecules to the cross-linked polymer of the membrane. The reaction is fast, can be carried out efficiently in aqueous media, works well at room temperature, and can be photo-initiated using a relatively long wavelength light (365 nm), which has very limited effect on protein bioactivity. In addition, it can allow for controlled biomolecule attachment, which can be advantageous in terms of preserving bioactivity and 3D structure of the biomolecule.

In certain embodiments, it is possible to immobilize onto the composite materials described herein any biomolecule that has free thiol functionality. This can be very useful in making bio-affinity membranes for bioseparation or biocatalysis membranes (by immobilizing enzyme(s)). In certain embodiments, the composite materials may be functionalized with oligonucleotide probes for DNA detection.

Porous Support Member

In some embodiments, the porous support member contains pores of average diameter of about 0.1 to about 50 μm.

In some embodiments, the porous support member has a volume porosity of about 40% to about 90%.

In certain embodiments, the porous support is flat.

In certain embodiments, the porous support is disk-shaped.

Many porous substrates or membranes can be used as the support member. In some embodiments, the porous support member is made of polymeric material. In certain embodiments, the support may be a polyolefin, which is available at low cost. In certain embodiments, the polyolefin may be poly(ethylene), poly(propylene), or poly(vinylidene difluoride). Extended polyolefin membranes made by thermally induced phase separation (TIPS), or non-solvent induced phase separation are mentioned. In certain embodiments, the support member may be made from natural polymers, such as cellulose or its derivatives. In certain embodiments, suitable supports include polyethersulfone membranes, poly (tetrafluoroethylene) membranes, nylon membranes, cellulose ester membranes, fiberglass, or filter papers.

In certain embodiments, the porous support is composed of woven or non-woven fibrous material, for example, a polyolefin, such as polypropylene. Such fibrous woven or non-woven support members can have pore sizes larger than the TIPS support members, in some instances up to about 75 μm. The larger pores in the support member permit formation of composite materials having larger macropores in the macroporous gel. Non-polymeric support members can also be used, such as ceramic-based supports. The porous support member can take various shapes and sizes.

In some embodiments, the support member is in the form of a membrane.

In some embodiments, the support member has a thickness from about 10 to about 2000 μm, from about 10 to about 1000 μm, or from about 10 to about 500 μm.

In other embodiments, multiple porous support units can be combined, for example, by stacking. In one embodiment, a stack of porous support membranes, for example, from 2 to 10 membranes, can be assembled before the gel is formed within the void of the porous support. In another embodiment, single support member units are used to form composite material membranes, which are then stacked before use.

Relationship Between Gel and Support Member

The gel may be anchored within the support member. The term "anchored" is intended to mean that the gel is held within the pores of the support member, but the term is not necessarily restricted to mean that the gel is chemically bound to the pores of the support member. The gel can be held by the physical constraint imposed upon it by enmeshing and intertwining with structural elements of the support member, without actually being chemically grafted to the support member, although in some embodiments, the gel may be grafted to the surface of the pores of the support member.

In certain embodiments, the cross-linked gels are macroporous. In these instances, because the macropores are present in the gel that occupies the pores of the support member, the macropores of the gel must be smaller than the pores of the support member. Consequently, the flow characteristics and separation characteristics of the composite material are dependent on the characteristics of the gel, but are largely independent of the characteristics of the porous support member, with the proviso that the size of the pores present in the support member is greater than the size of the macropores of the gel. The porosity of the composite material can be tailored by filling the support member with a gel whose porosity is partially or completely dictated by the nature and amounts of monomer or polymer, cross-linking agent, reaction solvent, and porogen, if used. Properties of the composite material are determined partially, if not entirely, by the properties of the gel. The net result is that the invention provides control over macropore-size, permeability and surface area of the composite materials.

When present, the number of macropores in the composite material is not dictated by the number of pores in the support material. The number of macropores in the composite material can be much greater than the number of pores in the support member because the macropores are smaller than the pores in the support member. As mentioned above, the effect of the pore-size of the support material on the pore-size of the macroporous gel is generally negligible. An exception is found in those cases where the support member has a large difference in pore-size and pore-size distribution, and where a macroporous gel having very small pore-sizes and a narrow range in pore-size distribution is sought. In these cases, large variations in the pore-size distribution of the support member are weakly reflected in the pore-size distribution of the macroporous gel. In certain embodiments, a support member with a somewhat narrow pore-size range may be used in these situations.

In certain embodiments, the invention relates to any one of the aforementioned composite materials, wherein the composite materials are relatively non-toxic.

Preparation of Composite Materials

In certain embodiments, the composite materials of the invention may be prepared by single-step methods. In certain embodiments, these methods may use water or other environmentally benign solvents as the reaction solvent. In certain embodiments, the methods may be rapid and, therefore, may lead to simple and/or rapid manufacturing processes. In certain embodiments, preparation of the composite materials may be inexpensive.

In certain embodiments, the composite materials may be prepared by mixing a monomer or monomers, a cross-linking agent or agents, an initiator or initiators, and optionally one or more porogens, in one or more suitable solvents. In certain embodiments, the resulting mixture may be homogeneous. In certain embodiments, the mixture may be heterogeneous. In certain embodiments, the mixture may then be introduced into a suitable porous support, where a gel forming reaction may take place.

In certain embodiments, a porogen may be added to the reactant mixture, wherein porogens may be broadly described as pore-generating additives. In certain embodiments, the porogen may be selected from the group consisting of thermodynamically poor solvents and extractable polymers (e.g., poly(ethyleneglycol)), surfactants, and salts.

In some embodiments, the gel forming reaction must be initiated. In certain embodiments, the gel forming reaction may be initiated by any known method, for example, through thermal activation or exposure to UV radiation. In certain embodiments, the reaction may be initiated by UV radiation in the presence of a photoinitiator. In certain embodiments, the photoinitiator may be selected from the group consisting of 2-hydroxy-1-[4-(2-hydroxyethoxy)phenyl]-2-methyl-1-propanone (Irgacure 2959), 4,4'-azobis(4-cyanovaleric acid) (ACVA), 2,2-dimethoxy-2-phenylacetophenone (DMPA), benzophenone, benzoin and benzoin ethers, such as benzoin ethyl ether and benzoin methyl ether, dialkoxyacetophenones, hydroxyalkylphenones, and $\alpha$-hydroxymethyl benzoin sulfonic esters. Thermal activation may require the addition of a thermal initiator. In certain embodiments, the thermal initiator may be selected from the group consisting of 1,1'-azobis(cyclohexanecarbonitrile) (VAZO® catalyst 88), azobis(isobutyronitrile) (AIBN), potassium persulfate, ammonium persulfate, and benzoyl peroxide.

In certain embodiments, the gel-forming reaction may be initiated by UV radiation. In certain embodiments, a photoinitiator may be added to the reactants of the gel forming reaction, and the support member containing the mixture of monomer, cross-linking agent, and photoinitiator may be exposed to UV radiation at wavelengths from about 250 nm to about 400 nm for a period of a few seconds to a few hours. In certain embodiments, the support member containing the mixture of monomer, cross-linking agent, and photoinitiator may be exposed to UV radiation at about 350 nm for a period of a few seconds to a few hours. In certain embodiments, the support member containing the mixture of monomer, cross-linking agent, and photoinitiator may be exposed to UV radiation at about 350 nm for about 10 minutes. In certain embodiments, visible wavelength light may be used to initiate the polymerization. In certain embodiments, the support member must have a low absorbance at the wavelength used so that the energy may be transmitted through the support member.

In certain embodiments, the rate at which polymerization is carried out may have an effect on the size of the macropores obtained in the macroporous gel. In certain embodiments, when the concentration of cross-linker in a gel is increased to sufficient concentration, the constituents of the gel begin to aggregate to produce regions of high polymer density and regions with little or no polymer, which latter regions are referred to as "macropores" in the present specification. This mechanism is affected by the rate of polymerization.

In certain embodiments, once the composite materials are prepared, they may be washed with various solvents to remove any unreacted components and any polymer or oligomers that are not anchored within the support. In certain embodiments, solvents suitable for the washing of the composite material include water, acidic (e.g., HCl) or basic (e.g., NaOH) aqueous solution, aqueous salt solutions (e.g., NaCl), acetone, methanol, ethanol, propanol, and DMF.

Exemplary Uses of the Composite Materials

In certain embodiments, the invention relates to a method, wherein a fluid is passed through the cross-linked gel of any one of the aforementioned composite materials. By tailoring the conditions for binding or fractionation, good selectivity can be obtained.

In certain embodiments, the invention relates to a method of separating biomolecules, such as proteins or immunoglobulins, from solution. In certain embodiments, the invention relates to a method of purifying biomolecules, such as proteins or immunoglobulins. In certain embodiments, the invention relates to a method of purifying proteins or monoclonal antibodies with high selectivity. In certain embodiments, the invention relates to a method, wherein the biological molecule or biological ion retains its tertiary or quaternary structure, which may be important in retaining biological activity. In certain embodiments, biological molecules or biological ions that may be separated or purified include proteins, such as albumins, e.g., bovine serum albumin, and lysozyme. In certain embodiments, biological molecules or biological ions that may be separated include γ-globulins of human and animal origins, immunoglobulins such as IgG, IgM, or IgE of human and animal origins, proteins of recombinant and natural origin including protein A, phytochrome, halophilic protease, poly(3-hydroxybutyrate) depolymerase, aculaecin-A acylase, polypeptides of synthetic and natural origin, interleukin-2 and its receptor, enzymes such as phosphatase, dehydrogenase, ribonuclease A, etc., monoclonal antibodies, fragments of antibodies, trypsin and its inhibitor, albumins of varying origins, e.g., α-lactalbumin, human serum albumin, chicken egg albumin, ovalbumin etc., cytochrome C, immunoglobulins, myoglobulin, recombinant human interleukin, recombinant fusion protein, nucleic acid derived products, DNA and RNA of synthetic and natural origin, DNA plasmids, lectin, α-chymotrypsinogen, and natural products including small molecules. In certain embodiments, the invention relates to a method of recovering an antibody fragment from variants, impurities, or contaminants associated therewith. In certain embodiments, biomolecule separation or purification may occur substantially in the cross-linked gel. In certain embodiments, biomolecule separation or purification may occur substantially in the macropores of the cross-linked gel, when the cross-linked gel has macropores.

In certain embodiments, the invention relates to a method of reversible adsorption of a substance. In certain embodiments, an adsorbed substance may be released by changing the liquid that flows through the gel. In certain embodiments, the uptake and release of substances may be controlled by variations in the composition of the cross-linked gel.

In certain embodiments, the invention relates to a method, wherein the substance may be applied to the composite material from a buffered solution.

In certain embodiments, the invention relates to a method, wherein the substance may be eluted using varying concentrations and pHs of aqueous salt solutions.

In certain embodiments, the invention relates to a method that exhibits high binding capacities. In certain embodiments, the invention relates to a method that exhibits binding capacities of about 1 $mg/mL_{membrane}$, about 2 $mg/mL_{membrane}$, about 3 $mg/mL_{membrane}$, about 4 $mg/mL_{membrane}$, about 5 $mg/mL_{membrane}$, about 6 $mg/mL_{membrane}$, about 7 $mg/mL_{membrane}$, about 8 $mg/mL_{membrane}$, about 9 $mg/mL_{membrane}$, about 10 $mg/mL_{membrane}$, about 12 $mg/mL_{membrane}$, about 14 $mg/mL_{membrane}$, about 16 $mg/mL_{membrane}$, about 18 $mg/mL_{membrane}$, about 20 $mg/mL_{membrane}$, about 30 $mg/mL_{membrane}$, about 40 $mg/mL_{membrane}$, about 50 $mg/mL_{membrane}$, about 60 $mg/mL_{membrane}$, about 70 $mg/mL_{membrane}$, about 80 $mg/mL_{membrane}$, about 90 $mg/mL_{membrane}$, about 100 $mg/mL_{membrane}$, about 110 $mg/mL_{membrane}$, about 120 $mg/mL_{membrane}$, about 130 $mg/mL_{membrane}$, about 140 $mg/mL_{membrane}$, about 150 $mg/mL_{membrane}$, about 160 $mg/mL_{membrane}$, about 170 $mg/mL_{membrane}$, about 180 $mg/mL_{membrane}$, about 190 $mg/mL_{membrane}$, about 200 $mg/mL_{membrane}$, about 210 $mg/mL_{membrane}$, about 220 $mg/mL_{membrane}$, about 230 $mg/mL_{membrane}$, about 240 $mg/mL_{membrane}$, about 250 $mg/mL_{membrane}$, about 260 $mg/mL_{membrane}$, about 270 $mg/mL_{membrane}$, about 280 $mg/mL_{membrane}$, about 290 $mg/mL_{membrane}$, about 300 $mg/mL_{membrane}$, about 320 $mg/mL_{membrane}$, about 340 $mg/mL_{membrane}$ $mg/mL_{membrane}$, about 360 $mg/mL_{membrane}$, about 380 $mg/mL_{membrane}$, or about 400 $mg/mL_{membrane}$ at 10% breakthrough.

The water flux, $Q_{H2O}$ (kg/m² h), was calculated using the following equation:

$$Q_{H_2O} = \frac{(m_1 - m_2)}{A \cdot t}$$

where $m_1$ is the mass of water transferred through the membrane at $t_1$, $m_2$ is the mass of water transferred through the membrane at $t_2$, A is the membrane cross-sectional area and t is the time (where $t_1 > t_2$).

In certain embodiments, an additive may be added to the eluting salt solution (the second fluid, or the third or later fluid). In certain embodiments, the additive is added in a low concentration (e.g., less than about 2 M, about 1 M, about 0.5 M, or about 0.2 M). In certain embodiments, the additive is a water-miscible alcohol, a detergent, dimethyl sulfoxide, dimethyl formamide, or an aqueous solution of a chaotropic salt.

In certain embodiments, changing pH is an effective elution tool for protein elution with or without changing the conductivity of the mobile phase.

Pore Size Determination

SEM and ESEM

As mentioned above, in certain embodiments, the cross-linked gel is a macroporous cross-linked gel. The average diameter of the macropores in the macroporous cross-linked gel may be estimated by one of many methods. One method that may be employed is scanning electron microscopy (SEM). SEM is a well-established method for determining pore sizes and porosities in general, and for characterizing membranes in particular. Reference is made to the book *Basic Principles of Membrane Technology* by Marcel Mulder (© 1996) ("Mulder"), especially Chapter IV. Mulder provides an overview of methods for characterizing membranes. For porous membranes, the first method mentioned is electron microscopy. SEM is a very simple and useful technique for characterising microfiltration membranes. A clear and concise picture of the membrane can be obtained in terms of the top layer, cross-section and bottom layer. In addition, the porosity and pore size distribution can be estimated from the photographs.

Environmental SEM (ESEM) is a technique that allows for the non-destructive imaging of specimens that are wet, by allowing for a gaseous environment in the specimen chamber. The environmental secondary detector (ESD) requires a gas background to function and operates at from about 3 torr to about 20 torr. These pressure restraints limit the ability to vary humidity in the sample chamber. For example, at 10 torr, the relative humidity at a specific temperature is as follows:

| Relative Humidity at 10 torr (%) | T (° C.) |
| --- | --- |
| About 80 | About 16 |
| About 70 | About 18 |
| About 60 | About 20 |
| About 40 | About 24 |
| About 20 | About 40 |
| About 10 | About 50 |
| About 2 | About 70 |
| About 1 | About 100 |

This is a useful guide to relative humidity in the sample chamber at different temperatures. In certain embodiments, the relative humidity in the sample chamber during imaging is from about 1% to about 99%. In certain embodiments, the relative humidity in the sample chamber during imaging is about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%. In certain embodiments, the relative humidity in the sample chamber during imaging is about 45%

In certain embodiments, the microscope has nanometer resolution and up to about 100,000× magnification.

In certain embodiments, the temperature in the sample chamber during imaging is from about 1° C. to about 95° C. In certain embodiments, the temperature in the sample chamber during imaging is about 2° C., about 3° C., about 4° C., about 5° C., about 6° C., about 7° C., about 8° C., about 9° C., about 10° C., about 12° C., about 14° C., about 16° C., about 18° C., about 20° C., about 25° C., about 30° C., about 35° C., about 40° C., about 45° C., about 50° C., about 55° C., about 60° C., about 65° C., about 70° C., about 75° C., about 80° C., or about 85° C. In certain embodiments, the temperature in the sample chamber during imaging is about 5° C.

In certain embodiments, the pressure in the sample chamber during imaging is from about 0.5 torr to about 20 torr. In certain embodiments, the pressure in the sample chamber during imaging is about 4 torr, about 6 torr, about 8 torr, about 10 torr, about 12 torr, about 14 torr, about 16 torr, about 18 torr, or about 20 torr. In certain embodiments, the pressure in the sample chamber during imaging is about 3 torr.

In certain embodiments, the working distance from the source of the electron beam to the sample is from about 6 mm to about 15 mm. In certain embodiments, the working distance from the source of the electron beam to the sample is about 6 mm, about 7 mm, about 8 mm, about 9 mm, about 10 mm, about 11 mm, about 12 mm, about 13 mm, about 14 mm, or about 15 mm. In certain embodiments, the working distance from the source of the electron beam to the sample is about 10 mm.

In certain embodiments, the voltage is from about 1 kV to about 30 kV. In certain embodiments, the voltage is about 2 kV, about 4 kV, about 6 kV, about 8 kV, about 10 kV, about 12 kV, about 14 kV, about 16 kV, about 18 kV, about 20 kV, about 22 kV, about 24 kV, about 26 kV, about 28 kV, or about 30 kV. In certain embodiments, the voltage is about 20 kV.

In certain embodiments, the average pore diameter may be measured by estimating the pore diameters in a representative sample of images from the top or bottom of a composite material. One of ordinary skill in the art will recognize and acknowledge various experimental variables associated with obtaining an ESEM image of a wetted membrane, and will be able to design an experiment accordingly.

Capillary Flow Porometry

Capillary flow porometry is an analytical technique used to measure the pore size(s) of porous materials. In this analytical technique, a wetting liquid is used to fill the pores of a test sample and the pressure of a non-reacting gas is used to displace the liquid from the pores. The gas pressure and flow rate through the sample is accurately measured and the pore diameters are determined using the following equation: The gas pressure required to remove liquid from the pores is related to the size of the pore by the following equation:

$$D = 4 \times \gamma \cdot \cos \theta / P$$

D=pore diameter
γ=liquid surface tension
θ=liquid contact angle
P=differential gas pressure This equation shows that the pressure required to displace liquid from the wetted sample is inversely related to the pore size. Since this technique involves the flow of a liquid from the pores of the test sample under pressure, it is useful for the characterization of "through pores" (interconnected pores that allow fluid flow from one side of the sample to the other). Other pore types (closed and blind pores) are not detectable by this method.

Capillary flow porometry detects the presence of a pore when gas starts flowing through that pore. This occurs only when the gas pressure is high enough to displace the liquid from the most constricted part of the pore. Therefore, the pore diameter calculated using this method is the diameter of the pore at the most constricted part and each pore is detected as a single pore of this constricted diameter. The largest pore diameter (called the bubble point) is determined by the lowest gas pressure needed to initiate flow through a wet sample and a mean pore diameter is calculated from the mean flow pressure. In addition, both the constricted pore diameter range and pore size distribution may be determined using this technique.

This method may be performed on small membrane samples (e.g., about 2.5 cm diameter) that are immersed in a test fluid (e.g., water, buffer, alcohol). The range of gas pressure applied can be selected from about 0 to about 500 psi.

Other Methods of Determining Pore Diameter

Mulder describes other methods of characterizing the average pore size of a porous membrane, including atomic force microscopy (AFM) (page 164), permeability calculations (page 169), gas adsorption-desorption (page 173), thermoporometry (page 176), permporometry (page 179), and liquid displacement (page 181). Mulder, and the references cited therein, are hereby incorporated by reference.

Exemplary Composite Materials

In certain embodiments, the invention relates to a composite material, comprising:

a support member, comprising a plurality of pores extending through the support member; and a cross-linked gel, wherein the cross-linked gel comprises a polymer derived from a first monomer and a first cross-linker;

wherein the cross-linked gel is located in the pores of the support member;

the first monomer comprises two thiol functional groups; and the first cross-linker comprises (i) at least three carbon-carbon double bonds, (ii) at least two carbon-carbon triple bonds, or (iii) at least one carbon-carbon triple bond and at least one carbon-carbon double bond.

In certain embodiments, the invention relates to a composite material, comprising:

a support member, comprising a plurality of pores extending through the support member; and a cross-linked gel, wherein the cross-linked gel comprises a polymer derived from a first monomer, a second monomer, and a first cross-linker;

wherein
the cross-linked gel is located in the pores of the support member;
the first monomer comprises two thiol functional groups;
the second monomer comprises two carbon-carbon double bonds; and
the first cross-linker comprises (i) at least three thiol functional groups, (ii) at least three carbon-carbon double bonds, (iii) at least two carbon-carbon triple bonds, or (iv) at least one carbon-carbon triple bond and at least one carbon-carbon double bond.

In certain embodiments, the invention relates to any one of the aforementioned composite materials, wherein the cross-linked gel is macroporous.

In certain embodiments, the invention relates to any one of the aforementioned composite materials, wherein the first monomer comprises two terminal thiol functional groups.

In certain embodiments, the invention relates to any one of the aforementioned composite materials, wherein the first monomer is substantially soluble in DMAc or DPMA, or a mixture thereof.

In certain embodiments, the invention relates to any one of the aforementioned composite materials, wherein the first monomer is 2,2'-(ethylenedioxy)diethanethiol (EDDET), 1,2-ethanedithiol, 1,4-butanedithiol, PEG dithiol (such as linear PEG dithiol), 1,6-hexanedithiol, 2,2'-thiodiethanethiol, ethane-1,2-diyl bis(3-mercaptopropanoate), hexa(ethylene glycol) dithiol, tetra(ethylene glycol) dithiol, 1,16-hexadecanedithiol, benzene-1,2-dithiol, benzene-1,3-dithiol, benzene-1,4-dithiol, biphenyl-4,4'-dithiol, p-terphenyl-4,4"-dithiol, (S)-2-aminobutane-1,4-dithiol hydrochloride, 4-phenyl-4H-(1,2,4)tri azole-3,5-dithiol, 5-(4-chlorophenyl)-pyrimidine-4,6-dithiol, 1,4-benzenedimethanethiol, 2-mercaptoethyl ether, or L-(−)-dithiothreitol.

In certain embodiments, the invention relates to any one of the aforementioned composite materials, wherein the second monomer comprises two terminal carbon-carbon double bonds.

In certain embodiments, the invention relates to any one of the aforementioned composite materials, wherein the second monomer is substantially soluble in DMAc or DPMA, or a mixture thereof.

In certain embodiments, the invention relates to any one of the aforementioned composite materials, wherein the second monomer is tri(ethylene glycol) divinyl ether (TEGDV), 1,9-decadiene, 1,4-bis(vinyloxy)butane, diallylphthalate, diallyl diglycol carbonate, poly(ethylene glycol) divinyl ether, divinyl glycol, or divinylbenzene, divinyl sulfone, 1,4-butanediol divinyl ether, allyl ether, allyl sulfide, 1,4-bis(4-vinylphenoxy)butane, 1,5-hexadiene, dipentene, (R)-(+)-limonene, (S)-(−)-limonene, N,N'-methylenebis(acrylamide), or N,N'-ethylenebis(acrylamide).

In certain embodiments, the invention relates to any one of the aforementioned composite materials, wherein the mole ratio of first monomer to second monomer is greater than 1:1, for example about 1.5:1, about 2:1, about 2.5:1, about 3:1, about 3.5:1, about 4:1, about 4.5:1, or about 5:1.

In certain embodiments, the invention relates to any one of the aforementioned composite materials, wherein the composite material further comprises a third monomer, wherein the third monomer comprises two carbon-carbon double bonds.

In certain embodiments, the invention relates to any one of the aforementioned composite materials, wherein the third monomer comprises two terminal carbon-carbon double bonds.

In certain embodiments, the invention relates to any one of the aforementioned composite materials, wherein the third monomer is substantially soluble in DMAc or DPMA, or a mixture thereof.

In certain embodiments, the invention relates to any one of the aforementioned composite materials, wherein the third monomer is (+)-N,N'-diallyltartramide (DATA), diallyl disulfide, diallyl carbonate, diallyl maleate, diallyl succinate, trimethylolpropane diallyl ether, 1,1-diallyl-1-docosanol, 1,1-diallyl-3-(1-naphthyl)urea, 1,1-diallyl-3-(2-ethylphenyl)urea, 1,2-diallyl-1,2-cyclohexanediol, 2,6-diallyl-meta-cresol, N,N-diallyl-2-hydroxypropanamide, 1,4-pentadien-3-ol, trimethyl(propargyl)silane, or propargylamine.

In certain embodiments, the invention relates to any one of the aforementioned composite materials, wherein the mole ratio of first monomer to third monomer is from greater than 1:1, for example about 1.5:1, about 2:1, about 2.5:1, about 3:1, about 3.5:1, about 4:1, about 4.5:1, or about 5:1.

In certain embodiments, the invention relates to any one of the aforementioned composite materials, wherein the first cross-linker comprises at least three carbon-carbon double bonds.

In certain embodiments, the invention relates to any one of the aforementioned composite materials, wherein the first cross-linker comprises three carbon-carbon double bonds. In certain embodiments, the invention relates to any one of the aforementioned composite materials, wherein the first cross-linker comprises three terminal carbon-carbon double bonds.

In certain embodiments, the invention relates to any one of the aforementioned composite materials, wherein the first cross-linker comprises two carbon-carbon triple bonds. In certain embodiments, the invention relates to any one of the aforementioned composite materials, wherein the first cross-linker comprises two terminal carbon-carbon triple bonds.

In certain embodiments, the invention relates to any one of the aforementioned composite materials, wherein the first cross-linker is substantially soluble in DMAc or DPMA, or a mixture thereof.

In certain embodiments, the invention relates to any one of the aforementioned composite materials, wherein the first cross-linker is 1,3,5-triallyl-1,3, 5-triazine-2,4,6(1H,3H,5H)-trione (TATATO), 1,6-heptadiyne, 1,7-octadiyne, 1,8-nonadiyne, 1,9-decadiyne, propargyl acrylate, 4-arm PEG norbornene (Fairbanks, B. D., et al. Adv. Mater. 2009, 21 (48), 5005-5010), trimethylolpropane triacrylate, tetraalkyne poly(ethylene glycol) (e.g., Daniele, M. A., et al. Biomaterials 2014, 35, 1845-1856), 2,4,6-triallyloxy-1,3,5-triazine, triallylamine, triallyl borate, triallylphosphine, diallyl fumarate, 3-(allyloxy)-1-propyne, glyoxal bis(diallyl acetal), tetraallylsilane, propargyl ether, or squalene.

In certain embodiments, the invention relates to any one of the aforementioned composite materials, wherein the first cross-linker is trimethylolpropanetri(3-mercaptopropionate), pentaerythritol tetra(3-mercaptopropionate), poly(ethylene glycol) tetra-thiol (e.g., Daniele, M. A., et al. Biomaterials 2014, 35, 1845-1856), tris[2(3-mercaptopropionyl oxy)ethyl]isocyanurate, pentaerythritol tetrakis(2-mercaptoacetate), trithiocyanuric acid, or 1-thiohexitol.

In certain embodiments, the invention relates to any one of the aforementioned composite materials, wherein the composite material further comprises a second cross-linker; and the second cross-linker comprises (i) at least three thiol functional groups, (ii) at least three carbon-carbon double bonds, (iii) at least two carbon-carbon triple bonds, or (iv) at least one carbon-carbon triple bond and at least one carbon-carbon double bond.

In certain embodiments, the invention relates to any one of the aforementioned composite materials, wherein the second cross-linker comprises at least two carbon-carbon triple bonds.

In certain embodiments, the invention relates to any one of the aforementioned composite materials, wherein the second cross-linker comprises two carbon-carbon triple bonds. In certain embodiments, the invention relates to any one of the aforementioned composite materials, wherein the second cross-linker comprises two terminal carbon-carbon triple bonds.

In certain embodiments, the invention relates to any one of the aforementioned composite materials, wherein the second cross-linker is different from the first cross-linker.

In certain embodiments, the invention relates to any one of the aforementioned composite materials, wherein the second cross-linker is substantially soluble in DMAc or DPMA, or a mixture thereof.

In certain embodiments, the invention relates to any one of the aforementioned composite materials, wherein the second cross-linker is 1,3,5-triallyl-1,3,5-triazine-2,4,6(1H, 3H,5H)-trione (TATATO), 1,6-heptadiyne, 1,7-octadiyne, 1,8-nonadiyne, 1,9-decadiyne, propargyl acrylate, 2,4,6-triallyloxy-1,3,5-triazine, triallylamine, triallyl borate, triallylphosphine, diallyl fumarate, 3-(allyloxy)-1-propyne, dipropargylamine, 5,6-dimethyl-5-decen-1,9-diyne, glyoxal bis(diallyl acetal), tetraallyl silane, propargyl ether, squalene, trimethylolpropanetri(3-mercaptopropionate), pentaerythritol tetra(3-mercaptopropionate), poly(ethylene glycol) tetra-thiol, tris[2(3-mercaptopropionyloxy)ethyl]isocyanurate, pentaerythritol tetrakis(2-mercaptoacetate) trithiocyanuric acid, or 1-thiohexitol.

In certain embodiments, the invention relates to a composite material, comprising:
a support member, comprising a plurality of pores extending through the support member; and
a cross-linked gel, wherein the cross-linked gel comprises a polymer derived from a first monomer and a first cross-linker;
wherein
the cross-linked gel is located in the pores of the support member;
the first monomer comprises (i) two carbon-carbon double bonds, or (ii) a carbon-carbon triple bond; and
the first cross-linker comprises at least three thiol functional groups.

In certain embodiments, the invention relates to any one of the aforementioned composite materials, wherein the cross-linked gel is macroporous.

In certain embodiments, the invention relates to any one of the aforementioned composite materials, wherein the first monomer comprises two terminal carbon-carbon double bonds.

In certain embodiments, the invention relates to any one of the aforementioned composite materials, wherein the first monomer is substantially soluble in DMAc or DPMA, or a mixture thereof.

In certain embodiments, the invention relates to any one of the aforementioned composite materials, wherein the first monomer is tri(ethylene glycol) divinyl ether (TEGDV), 1,9-decadiene, 1,4-bis(vinyloxy)butane, diallylphthalate, diallyl diglycol carbonate, poly(ethylene glycol) divinyl ether, divinyl glycol, or divinylbenzene, divinyl sulfone, 1,4-butanediol divinyl ether, allyl ether, allyl sulfide, 1,4-bis(4-vinylphenoxy)butane, 1,5-hexadiene, dipentene, (R)-(+)-limonene, or (S)-(−)-limonene.

In certain embodiments, the invention relates to any one of the aforementioned composite materials, wherein the mole ratio of first monomer to second monomer is greater than 1:1, for example about 1.5:1, about 2:1, about 2.5:1, about 3:1, about 3.5:1, about 4:1, about 4.5:1, or about 5:1.

In certain embodiments, the invention relates to any one of the aforementioned composite materials, wherein the first cross-linker is substantially soluble in DMAc or DPMA, or a mixture thereof.

In certain embodiments, the invention relates to any one of the aforementioned composite materials, wherein the first cross-linker is trimethylolpropanetri(3-mercaptopropionate), pentaerythritol tetra(3-mercaptopropionate), poly(ethylene glycol) tetra-thiol (e.g., Daniele, M. A., et al. Biomaterials 2014, 35, 1845-1856), tris[2(3-mercaptopropionyloxy)ethyl]isocyanurate, pentaerythritol tetrakis(2-mercaptoacetate), trithiocyanuric acid, or 1-thiohexitol.

In certain embodiments, the invention relates to any one of the aforementioned composite materials, wherein the cross-linked gel further comprises a plurality of grafted end-groups. In certain embodiments, the invention relates to any one of the aforementioned composite materials, wherein the grafted end-groups are derived from a molecule having a thiol functional group or a molecule having an unsaturated carbon-carbon bond.

In certain embodiments, the invention relates to any one of the aforementioned composite materials, wherein the grafted end-groups are derived from a molecule having a thiol functional group or a molecule having an unsaturated carbon-carbon bond; and the molecule having a thiol functional group or the molecule having an unsaturated carbon-carbon bond has a log P from about 0.5 to about 8.0. In certain embodiments, composite materials having hydrophobic grafted end-groups are useful for hydrophobic interaction chromatography.

In certain embodiments, the invention relates to any one of the aforementioned composite materials, wherein the molecule having a thiol functional group and the molecule having an unsaturated carbon-carbon bond are substantially soluble in DMAc or DPMA, or a mixture thereof.

In certain embodiments, the invention relates to any one of the aforementioned composite materials, wherein the grafted end-groups are derived from a molecule having a thiol functional group; and the molecule having a thiol functional group is 3-mercaptopropionic acid, 1-mercaptosuccinic acid, a peptide having a cysteine residue, a protein having a cysteine residue (either a naturally occurring cysteine residue or an engineered cysteine residue, e.g., Protein A), cysteamine, 1-thiohexitol, poly(ethylene glycol) 2-mercaptoethyl ether acetic acid, poly(ethylene glycol) methyl ether thiol, 1-thioglycerol, 2-naphthalenethiol, biphenyl-4-thiol, 3-amino-1,2,4-triazole-5-thiol, 5-(trifluoromethyl)pyridine-2-thiol, 1-[2-(dimethylamino)ethyl]-1H-tetrazole-5-thiol, 1-propanethiol, 1-butanethiol, 1-pentanethiol, 1-hexanethiol, 1-octanethiol, 8-amino-1-octanethiol hydrochloride, 3,3,4,4,5,5,6,6,7,7,8,8,8-tridecafluoro-1-octanethiol, 8-mercapto-1-octanol, or γ-Glu-Cys.

In certain embodiments, the invention relates to any one of the aforementioned composite materials, wherein the grafted end-groups are derived from a molecule having an unsaturated carbon-carbon bond; and the molecule having an unsaturated carbon-carbon bond is 1-octene, 1-hexyne, 4-bromo-1-butene, allyldiphenylphosphine, allylamine, allyl alcohol, 3,4-dihydroxy-1-butene, 7-octene-1,2-diol, 3-allyloxy-1,2-propanediol, 3-butenoic acid, 3,4-dehydro-L- proline, vinyl laurate, 1-vinyl-2-pyrrolidinone, vinyl cinnamate, an acylamide, or an acrylate.

In certain embodiments, the invention relates to any one of the aforementioned composite materials wherein the cross-linked gel comprises macropores; and the macropores have an average pore diameter of about 10 nm to about 3000 nm. In certain embodiments, the diameter of the macropores is estimated by one of the techniques described herein. In certain embodiments, the diameter of the macropores is calculated by capillary flow porometry.

In certain embodiments, the invention relates to any one of the aforementioned composite materials, wherein the average pore diameter of the macropores is about 25 nm to about 1500 nm.

In certain embodiments, the invention relates to any one of the aforementioned composite materials, wherein the average pore diameter of the macropores is about 50 nm to about 1000 nm. In certain embodiments, the invention relates to any one of the aforementioned composite materials, wherein the average pore diameter of the macropores is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, or about 700 nm.

In certain embodiments, the invention relates to any one of the aforementioned composite materials, wherein the average pore diameter of the macropores is about 300 nm to about 400 nm.

In certain embodiments, the invention relates to any one of the aforementioned composite materials, wherein the composite material is a membrane.

In certain embodiments, the invention relates to any one of the aforementioned composite materials, wherein the support member has a void volume; and the void volume of the support member is substantially filled with the macroporous cross-linked gel.

In certain embodiments, the invention relates to any one of the aforementioned composite materials, wherein the support member comprises a polymer; the support member is about 10 µm to about 1000 µm thick; the pores of the support member have an average pore diameter of about 0.1 µm to about 25 µm. In certain embodiments, the support member has a volume porosity of about 40% to about 90%.

In certain embodiments, the invention relates to any one of the aforementioned composite materials, wherein the thickness of the support member is about 10 µm to about 1000 µm. In certain embodiments, the invention relates to any one of the aforementioned composite materials, wherein the thickness of the support member is about 10 µm to about 500 µm. In certain embodiments, the invention relates to any one of the aforementioned composite materials, wherein the thickness of the support member is about 30 µm to about 300 µm. In certain embodiments, the invention relates to any one of the aforementioned composite materials, wherein the thickness of the support member is about 30 µm, about 50 µm, about 100 µm, about 150 µm, about 200 µm, about 250 µm, or about 300 µm.

In certain embodiments, the invention relates to any one of the aforementioned composite materials, wherein the pores of the support member have an average pore diameter of about 0.1 µm to about 25 µm. In certain embodiments, the invention relates to any one of the aforementioned composite materials, wherein the pores of the support member have an average pore diameter of about 0.5 µm to about 15 µm. In certain embodiments, the invention relates to any one of the aforementioned composite materials, wherein the pores of the support member have an average pore diameter of about 0.5 µm, about 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, or about 15 µm.

In certain embodiments, the invention relates to any one of the aforementioned composite materials, wherein the support member has a volume porosity of about 40% to about 90%. In certain embodiments, the invention relates to any one of the aforementioned composite materials, wherein the support member has a volume porosity of about 50% to about 80%. In certain embodiments, the invention relates to any one of the aforementioned composite materials, wherein the support member has a volume porosity of about 50%, about 60%, about 70%, or about 80%.

In certain embodiments, the invention relates to any one of the aforementioned composite materials, wherein the support member comprises a polyolefin.

In certain embodiments, the invention relates to any one of the aforementioned composite materials, wherein the support member comprises a polymeric material selected from the group consisting of polysulfones, polyethersulfones, polyphenyleneoxides, polycarbonates, polyesters, cellulose and cellulose derivatives.

In certain embodiments, the invention relates to any one of the aforementioned composite materials, wherein the support member comprises a fibrous woven or non-woven fabric comprising a polymer; the support member is from about 10 µm to about 2000 µm thick; the pores of the support member have an average pore diameter of from about 0.1 µm to about 25 µm; and the support member has a volume porosity of about 40% to about 90%.

In certain embodiments, the invention relates to any one of the aforementioned composite materials, wherein the composite material has a water contact angle from about 50° to about 120°.

Exemplary Methods of Use

In certain embodiments, the invention relates to a method, comprising the step of:

contacting at a first flow rate a first fluid comprising a substance with any one of the aforementioned composite materials, thereby adsorbing or absorbing a portion of the substance onto the composite material.

In certain embodiments, the first fluid further comprises a fragmented antibody, aggregated antibodies, a host cell protein, a polynucleotide, an endotoxin, or a virus.

In certain embodiments, the invention relates to any one of the aforementioned methods, wherein the fluid flow path of the first fluid is substantially through the macropores of the composite material.

In certain embodiments, the invention relates to any one of the aforementioned methods, wherein the fluid flow path of the first fluid is substantially perpendicular to the macropores of the composite material.

In certain embodiments, the invention relates to any one of the aforementioned methods, further comprising the step of:

contacting at a second flow rate a second fluid with the substance adsorbed or absorbed onto the composite material, thereby releasing a first portion of the substance from the composite material.

In certain embodiments, the invention relates to any one of the aforementioned methods, wherein the fluid flow path of the second fluid is substantially through the macropores of the composite material.

In certain embodiments, the invention relates to any one of the aforementioned methods, wherein the fluid flow path of the second fluid is substantially perpendicular to the macropores of the composite material.

In certain embodiments, the invention relates to any one of the aforementioned methods, further comprising the step of:

contacting at a third flow rate a third fluid with the substance adsorbed or absorbed onto the composite material, thereby releasing a second portion of the substance from the composite material.

In certain embodiments, the invention relates to any one of the aforementioned methods, wherein the substance is a biological molecule, biological ion, virus, or virus particle.

In certain embodiments, the invention relates to any one of the aforementioned methods, wherein the substance is a biological molecule or biological ion selected from the group consisting of albumins, lysozyme, viruses, cells, γ-globulins of human and animal origins, immunoglobulins of human and animal origins, proteins of recombinant and natural origins, polypeptides of synthetic and natural origins, interleukin-2 and its receptor, enzymes, monoclonal antibodies, trypsin and its inhibitor, cytochrome C, myoglobin, myoglobulin, α-chymotrypsinogen, recombinant human interleukin, recombinant fusion protein, nucleic acid derived products, DNA of synthetic and natural origins, and RNA of synthetic and natural origins.

In certain embodiments, the invention relates to any one of the aforementioned methods, wherein the biological molecule or biological ion is lysozyme, hIgG, myoglobin, human serum albumin, soy trypsin inhibitor, transferring, enolase, ovalbumin, ribonuclease, egg trypsin inhibitor, cytochrome c, Annexin V, or α-chymotrypsinogen.

In certain embodiments, the invention relates to any one of the aforementioned methods, wherein the first fluid is a buffer. In certain embodiments, the invention relates to any one of the aforementioned methods, wherein the concentration of the buffer in the first fluid is about 5 mM, about 10 mM, about 15 mM, about 20 mM, about 25 mM, about 30 mM, about 35 mM, about 40 mM, about 50 mM, about 60 mM, about 70 mM, about 75 mM, about 80 mM, about 85 mM, about 90 mM, about 95 mM, about 0.1 M, about 0.11 M, about 0.12 M, about 0.13 M, about 0.14 M, about 0.15 M, about 0.16 M, about 0.17 M, about 0.18 M, about 0.19 M or about 0.2 M. In certain embodiments, the invention relates to any one of the aforementioned methods, wherein the pH of the first fluid is about 5, about 5.5, about 6, about 6.5, about 7, about 7.5, about 8, about 8.5, or about 9.

In certain embodiments, the invention relates to any one of the aforementioned methods, wherein the first fluid comprises sodium phosphate.

In certain embodiments, the invention relates to any one of the aforementioned methods, wherein the first fluid comprises a salt. In certain embodiments, the invention relates to any one of the aforementioned methods, wherein the concentration of the salt in the first fluid is about about 50 mM, about 60 mM, about 70 mM, about 75 mM, about 80 mM, about 85 mM, about 90 mM, about 95 mM, about 0.1 M, about 0.11 M, about 0.12 M, about 0.13 M, about 0.14 M, about 0.15 M, about 0.16 M, about 0.17 M, about 0.18 M, about 0.19 M about 0.2 M, about 0.25 M, or about 0.3 M. In certain embodiments, the invention relates to any one of the aforementioned methods, wherein the salt is sodium chloride.

In certain embodiments, the invention relates to any one of the aforementioned methods, wherein the concentration of the substance in the first fluid is about 0.2 mg/mL to about 10 mg/mL. In certain embodiments, the invention relates to any one of the aforementioned methods, wherein the concentration of the substance in the first fluid is about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/L, about 1 mg/mL, about 1.2 mg/mL, about 1.4 mg/mL, about 1.6 mg/mL, about 1.8 mg/mL, about 2 mg/mL, about 3 mg/mL, about 4 mg/mL, about 5 mg/mL, about 6 mg/mL, about 7 mg/mL, about 8 mg/mL, about mg/mL, or about 10 mg/mL.

In certain embodiments, the invention relates to any one of the aforementioned methods, wherein the first flow rate is about 3 membrane volumes (MV)/min to about 70 MV/min. In certain embodiments, the invention relates to any one of the aforementioned methods, wherein the first flow rate is about 5 MV/min to about 30 MV/min. In certain embodiments, the invention relates to any one of the aforementioned methods, wherein the first flow rate is about 10 MV/min to about 20 MV/min. In certain embodiments, the invention relates to any one of the aforementioned methods, wherein the first flow rate is about 10 MV/min, about 11 MV/min, about 12 MV/min, about 13 MV/min, about 14 MV/min, about 15 MV/min, about 16 MV/min, about 17 MV/min, about 18 MV/min, about 19 MV/min, or about 20 MV/min.

In certain embodiments, the invention relates to any one of the aforementioned methods, wherein the first flow rate is about 0.5 mL/min to about 50 L/min. In certain embodiments, the invention relates to any one of the aforementioned methods, wherein the first flow rate is about 0.5 mL/min to about 25 L/min. In certain embodiments, the invention relates to any one of the aforementioned methods, wherein the first flow rate is about 0.5 mL/min to about 10 L/min. In certain embodiments, the invention relates to any one of the aforementioned methods, wherein the first flow rate is about 0.5 mL/min to about 1 L/min. In certain embodiments, the invention relates to any one of the aforementioned methods, wherein the first flow rate is about 0.5 mL/min to about 0.5 L/min. In certain embodiments, the invention relates to any one of the aforementioned methods, wherein the first flow rate is about 0.5 mL/min to about 100 mL/min. In certain embodiments, the invention relates to any one of the aforementioned methods, wherein the first flow rate is about 0.5 mL/min to about 10 mL/min. In certain embodiments, the invention relates to any one of the aforementioned methods, wherein the first flow rate is about 0.5 mL/min to about 2 mL/min. In certain embodiments, the invention relates to any one of the aforementioned methods, wherein the first flow rate is about 0.5 mL/min, about 0.6 mL/min, about 0.7 mL/min, about 0.8 mL/min, about 0.9 mL/min, about 1 mL/min, about 1.1 mL/min, about 1.2 mL/min, about 1.3 mL/min, about 1.4 mL/min, about 1.5 mL/min, about 1.6 mL/min, about 1.7 mL/min, or about 1.8 mL/min.

In certain embodiments, the invention relates to any one of the aforementioned methods, wherein the second fluid is a buffer. In certain embodiments, the invention relates to any one of the aforementioned methods, wherein the second fluid comprises glycine-HCl or sodium citrate. In certain embodiments, the invention relates to any one of the aforementioned methods, wherein the second fluid comprises glycine-HCl or sodium citrate in a concentration of about 5 mM to about 2 M. In certain embodiments, the invention relates to any one of the aforementioned methods, wherein the second fluid comprises glycine-HCl or sodium citrate in about 5 mM, about 10 mM, about 20 mM, about 30 mM, about 40 mM, about 50 mM, about 60 mM, about 70 mM, about 80 mM, about 90 mM, about 100 mM, about 125 mM, about 150 mM, about 200 mM, about 300 mM, or about 400 mM.

In certain embodiments, the invention relates to any one of the aforementioned methods, wherein the pH of the second fluid is about 2 to about 8. In certain embodiments, the invention relates to any one of the aforementioned methods, wherein the pH of the second fluid is about 2, about 2.2, about 2.4, about 2.6, about 2.8, about 3, about 3.2, about 3.4, about 3.6, about 3.8, about 4, about 4.2, about 4.4, about 4.6, about 4.8, about 5, about 5.2, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

In certain embodiments, the invention relates to any one of the aforementioned methods, wherein the second flow rate is about 3 membrane volumes (MV)/min to about 70 MV/min. In certain embodiments, the invention relates to any one of the aforementioned methods, wherein the second flow rate is about 5 MV/min to about 30 MV/min. In certain embodiments, the invention relates to any one of the aforementioned methods, wherein the second flow rate is about 10 MV/min to about 20 MV/min. In certain embodiments, the invention relates to any one of the aforementioned methods, wherein the second flow rate is about 10 MV/min, about 11 MV/min, about 12 MV/min, about 13 MV/min, about 14 MV/min, about 15 MV/min, about 16 MV/min, about 17 MV/min, about 18 MV/min, about 19 MV/min, or about 20 MV/min.

In certain embodiments, the invention relates to any one of the aforementioned methods, wherein the second flow rate is about 0.5 mL/min to about 50 L/min. In certain embodiments, the invention relates to any one of the aforementioned methods, wherein the second flow rate is about 0.5 mL/min to about 25 L/min. In certain embodiments, the invention relates to any one of the aforementioned methods, wherein the second flow rate is about 0.5 mL/min to about 10 L/min. In certain embodiments, the invention relates to any one of the aforementioned methods, wherein the second flow rate is about 0.5 mL/min to about 1 L/min. In certain embodiments, the invention relates to any one of the aforementioned methods, wherein the second flow rate is about 0.5 mL/min to about 0.5 L/min. In certain embodiments, the invention relates to any one of the aforementioned methods, wherein the second flow rate is about 0.5 mL/min to about 100 mL/min. In certain embodiments, the invention relates to any one of the aforementioned methods, wherein the second flow rate is about 0.5 mL/min to about 10 mL/min. In certain embodiments, the invention relates to any one of the aforementioned methods, wherein the second flow rate is about 0.5 mL/min to about 2 mL/min. In certain embodiments, the invention relates to any one of the aforementioned methods, wherein the second flow rate is about 0.5 mL/min, about 0.6 mL/min, about 0.7 mL/min, about 0.8 mL/min, about 0.9 mL/min, about 1 mL/min, about 1.1 mL/min, about 1.2 mL/min, about 1.3 mL/min, about 1.4 mL/min, about 1.5 mL/min, about 1.6 mL/min, about 1.7 mL/min, or about 1.8 mL/min.

In certain embodiments, the invention relates to any one of the aforementioned methods, further comprising the steps of:
cleaning the composite material; and
repeating the above-mentioned steps.

In certain embodiments, the invention relates to any one of the aforementioned methods, wherein the composite material is cleaned with a basic solution. In certain embodiments, the invention relates to any one of the aforementioned methods, wherein the composite material is cleaned with a fourth fluid; and the fourth fluid comprises sodium hydroxide.

In certain embodiments, the invention relates to any one of the aforementioned methods, wherein substantially all of the substance is adsorbed or absorbed onto the composite material.

In certain embodiments, the invention relates to a method, comprising the step of:
contacting at a first flow rate a first fluid comprising a substance and an unwanted material with any one of the aforementioned composite materials, thereby adsorbing or absorbing a portion of the unwanted material onto the composite material.

In certain embodiments, the invention relates to any one of the aforementioned methods, wherein the unwanted material comprises a fragmented antibody, aggregated antibodies, a host cell protein, a polynucleotide, an endotoxin, or a virus.

In certain embodiments, the invention relates to any one of the aforementioned methods, wherein substantially all of the unwanted material is adsorbed or absorbed onto the composite material.

In certain embodiments, the invention relates to any one of the aforementioned methods, wherein the fluid flow path of the first fluid is substantially through the macropores of the composite material.

In certain embodiments, the invention relates to any one of the aforementioned methods, wherein the substance is a biological molecule or biological ion.

In certain embodiments, the invention relates to any one of the aforementioned methods, wherein the biological molecule or biological ion is selected from the group consisting of albumins, lysozyme, viruses, cells, $\gamma$-globulins of human and animal origins, immunoglobulins of human and animal origins, proteins of recombinant and natural origins, polypeptides of synthetic and natural origins, interleukin-2 and its receptor, enzymes, monoclonal antibodies, trypsin and its inhibitor, cytochrome C, myoglobin, myoglobulin, $\alpha$-chymotrypsinogen, recombinant human interleukin, recombinant fusion protein, nucleic acid derived products, DNA of synthetic and natural origins, and RNA of synthetic and natural origins.

In certain embodiments, the invention relates to any one of the aforementioned methods, wherein the biological molecule or biological ion is lysozyme, hIgG, myoglobin, human serum albumin, soy trypsin inhibitor, transferring, enolase, ovalbumin, ribonuclease, egg trypsin inhibitor, cytochrome c, Annexin V, or $\alpha$-chymotrypsinogen.

In certain embodiments, the invention relates to any one of the aforementioned methods, wherein the first fluid is a clarified cell culture supernatant.

Exemplary Methods of Making

In certain embodiments, the invention relates to a method of making a composite material, comprising the steps of:
combining a first monomer, a first cross-linker, a photoinitiator, and a first solvent, wherein the first monomer comprises two thiol functional groups; and the first cross-linker comprises (i) at least three carbon-carbon double bonds, (ii) at least two carbon-carbon triple bonds, or (iii) at least one carbon-carbon triple bond and at least one carbon-carbon double bond, thereby forming a monomeric mixture;
contacting a support member with the monomeric mixture, thereby forming a modified support member; wherein the support member comprises a plurality of pores extending through the support member, and the average pore diameter of the pores is about 0.1 to about 25 µm;

covering the modified support member with a polymeric sheet, thereby forming a covered support member; and irradiating the covered support member for a period of time, thereby forming a composite material.

In certain embodiments, the invention relates to a method of making a composite material, comprising the steps of:

combining a first monomer, a second monomer, a first cross-linker, a photoinitiator, and a first solvent, thereby forming a monomeric mixture; wherein the first monomer comprises two thiol functional groups; the second monomer comprises two carbon-carbon double bonds; and the first cross-linker comprises (i) at least three thiol functional groups, (ii) at least three carbon-carbon double bonds, (iii) at least two carbon-carbon triple bonds, or (iv) at least one carbon-carbon triple bond and at least one carbon-carbon double bond;

contacting a support member with the monomeric mixture, thereby forming a modified support member; wherein the support member comprises a plurality of pores extending through the support member, and the average pore diameter of the pores is about 0.1 to about 25 µm;

covering the modified support member with a polymeric sheet, thereby forming a covered support member; and irradiating the covered support member for a period of time, thereby forming a composite material.

In certain embodiments, the invention relates to any one of the aforementioned methods, further comprising the step of washing the composite material with a second solvent, thereby forming a washed composite material. In certain embodiments, the second solvent is water.

In certain embodiments, the invention relates to any one of the aforementioned methods, further comprising the step of removing any excess monomeric mixture from the covered support member.

In certain embodiments, the invention relates to any one of the aforementioned methods, wherein the composite material is any one of the aforementioned composite materials.

In certain embodiments, the invention relates to any one of the aforementioned methods, wherein the monomeric mixture further comprises a plurality of end-group precursors; and the end-group precursors are molecules having a thiol functional group or molecules having an unsaturated carbon-carbon bond.

In certain embodiments, the invention relates to any one of the aforementioned methods, further comprising the steps of:

contacting the composite material with a mixture comprising a photoinitiator and a plurality of end-group precursors, thereby forming a grafting mixture; wherein the end-group precursors are molecules having a thiol functional group or molecules having an unsaturated carbon-carbon bond; and irradiating the grafting mixture for a period of time, thereby forming a modified composite material.

In certain embodiments, the invention relates to any one of the aforementioned methods, wherein the end-group precursor has a log P from about 0.5 to about 8.0.

In certain embodiments, the invention relates to any one of the aforementioned methods, wherein the end-group precursor is substantially soluble in DMAc or DPMA, or a mixture thereof.

In certain embodiments, the invention relates to any one of the aforementioned methods, wherein the end-group precursor is a molecule having a thiol functional group; and the molecule having a thiol functional group is 3-mercaptopropionic acid, 1-mercaptosuccinic acid, a peptide having a cysteine residue, a protein having a cysteine residue, cysteamine, 1-thiohexitol, poly(ethylene glycol) 2-mercaptoethyl ether acetic acid, poly(ethylene glycol) methyl ether thiol, 1-thioglycerol, 2-naphthalenethiol, biphenyl-4-thiol, 3-amino-1,2,4-triazole-5-thiol, 5-(trifluoromethyl)pyridine-2-thiol, 1-[2-(dimethylamino)ethyl]-1H-tetrazole-5-thiol, 1-propanethiol, 1-butanethiol, 1-pentanethiol, 1-hexanethiol, 1-octanethiol, 8-amino-1-octanethiol hydrochloride, 3,3,4,4,5,5,6,6,7,7,8,8,8-tridecafluoro-1-octanethiol, 8-mercapto-1-octanol, or γ-Glu-Cys.

In certain embodiments, the invention relates to any one of the aforementioned methods, wherein the end-group precursor is derived from a molecule having an unsaturated carbon-carbon bond; and the molecule having an unsaturated carbon-carbon bond is 1-octene, 1-hexyne, 4-bromo-1-butene, allyldiphenylphosphine, allylamine, allyl alcohol, 3,4-dihydroxy-1-butene, 7-octene-1,2-diol, 3-allyloxy-1,2-propanediol, 3-butenoic acid, 3,4-dehydro-L-proline, vinyl laurate, 1-vinyl-2-pyrrolidinone, vinyl cinnamate, an acylamide, or an acrylate.

In certain embodiments, the invention relates to any one of the aforementioned methods, wherein the ratio of reactive thiol groups to reactive alkene groups (where an alkyne group is equivalent to two alkene groups) in the monomeric mixture is from about 1:10 to about 2:1, for example, about 1:10, about 1:9, about 1:8, about 1:7, about 1:6, about 1:5, about 1:4, about 1:3, about 1:2, about 1:1, or about 2:1.

In certain embodiments, the invention relates to any one of the aforementioned methods, wherein the first monomer is present in the monomeric mixture in an amount from about 5% to about 25% by weight of the monomeric mixture. In certain embodiments, the invention relates to any one of the aforementioned methods, wherein the first monomer is present in the monomeric mixture in an amount from about 5% to about 20% by weight of the monomeric mixture.

In certain embodiments, the invention relates to any one of the aforementioned methods, wherein the second monomer is present in the monomeric mixture in an amount from about 0.1% to about 20% by weight of the monomeric mixture.

In certain embodiments, the invention relates to any one of the aforementioned methods, wherein the first cross-linker is present in the monomeric mixture in an amount from about 1% to about 20% by weight of the monomeric mixture.

In certain embodiments, the invention relates to any one of the aforementioned methods, wherein the photoinitiator is present in the monomeric mixture in an amount from about 0.1% to about 2% by weight of the monomeric mixture.

In certain embodiments, the invention relates to any one of the aforementioned methods, wherein the photoinitiator is benzoin or a benzoin ether, benzophenone, a dialkoxyacetophenone, 2,2-dimethoxy-2-phenylacetophenone, diphenyl (2,4,6-trimethylbenzoyl)phosphine oxide, a hydroxyalkylphenone, 1-hydroxy-cyclohexyl-phenyl-ketone, 4-(2-hydroxyethoxy)phenyl-(2-hydroxy-2-propyl)ketone, 1-[4-(2-hydroxyethoxy)-phenyl]-2-hydroxy-2-methyl-1-propane-1-one, 2-hydroxy-1-[4-(2-hydroxyethoxy)phenyl]-2-methyl-1-propanone, a α-hydroxymethyl benzoin sulfonic ester, 2-hydroxy-2-methylpropiophenone, lithium acylphosphinate, or 2-methyl-1-[4-(methylthio)phenyl]-2-(4-morpholinyl)-1-propanone, 4,4'-azobis(4-cyanovaleric acid) (ACVA), or a mixture thereof.

In certain embodiments, the invention relates to any one of the aforementioned methods, wherein the first solvent comprises N,N'-dimethylacetamide (DMAc), (±)-1,3-butanediol (Budiol), di(propylene glycol)methyl ether acetate (DPMA), water, di(propylene glycol) dimethyl ether (DPM), di(propylene glycol) propyl ether (DPGPE), di(propylene glycol) methyl ether (DPGME), tri(propylene glycol) butyl ether (TPGBE), 3-methyl-1,3-butanediol, 3,3-dimethyl-1,2-butanediol, 3-methoxy-1-butanol, dimethyl sulfoxide (DMSO), ethylene glycol, di(ethylene glycol), tri (ethylene glycol), tetra(ethylene glycol), hexylene glycol, sodium dodecyl sulfate, or N,N-dimethylformamide (DMF), or a mixture thereof.

In certain embodiments, the invention relates to any one of the aforementioned methods, wherein N,N'-dimethylacetamide (DMAc) is present in the monomeric mixture in an amount from about 0% to about 70% by weight of the monomeric mixture. In certain embodiments, the invention relates to any one of the aforementioned methods, wherein N,N'-dimethylacetamide (DMAc) is present in the monomeric mixture in an amount from about 0% to about 50% by weight of the monomeric mixture. In certain embodiments, the invention relates to any one of the aforementioned methods, wherein N,N'-dimethylacetamide (DMAc) is present in the monomeric mixture in an amount from about 0% to about 70% by weight of the total solvents. In certain embodiments, the invention relates to any one of the aforementioned methods, wherein N,N'-dimethylacetamide (DMAc) is present in the monomeric mixture in an amount from about 0% to about 50% by weight of the total solvents.

In certain embodiments, the invention relates to any one of the aforementioned methods, wherein (±)-1,3-butanediol (Budiol) is present in the monomeric mixture in an amount from about 0% to about 50% by weight of the monomeric mixture. In certain embodiments, the invention relates to any one of the aforementioned methods, wherein (±)-1,3-butanediol (Budiol) is present in the monomeric mixture in an amount from about 0% to about 50% by weight of the total solvents.

In certain embodiments, the invention relates to any one of the aforementioned methods, wherein di(propylene glycol)methyl ether acetate (DPMA) is present in the monomeric mixture in an amount from about 0% to about 60% by weight of the monomeric mixture. In certain embodiments, the invention relates to any one of the aforementioned methods, wherein di(propylene glycol)methyl ether acetate (DPMA) is present in the monomeric mixture in an amount from about 0% to about 60% by weight of the total solvents.

In certain embodiments, the invention relates to any one of the aforementioned methods, wherein water is present in the monomeric mixture in an amount from about 0% to about 50% by weight of the monomeric mixture. In certain embodiments, the invention relates to any one of the aforementioned methods, wherein water is present in the monomeric mixture in an amount from about 0% to about 30% by weight of the monomeric mixture. In certain embodiments, the invention relates to any one of the aforementioned methods, wherein water is present in the monomeric mixture in an amount from about 0% to about 30% by weight of the total solvents.

In certain embodiments, the invention relates to any one of the aforementioned methods, wherein the covered support member is irradiated at about 350 nm.

In certain embodiments, the invention relates to any one of the aforementioned methods, wherein the period of time is about 1 minute, about 5 minutes, about 10 minutes, about 15 minutes, about 20 minutes, about 30 minutes, about 45 minutes, or about 1 hour.

In certain embodiments, the invention relates to any one of the aforementioned methods, wherein the composite material comprises macropores.

In certain embodiments, the invention relates to any one of the aforementioned methods, wherein the average pore diameter of the macropores is less than the average pore diameter of the pores.

EXEMPLIFICATION

The following examples are provided as illustrations. It will be understood, however, that the specific details given in each example have been selected for purpose of illustration and are not to be construed as limiting the scope of the disclosure. Generally, the experiments were conducted under similar conditions unless noted.

General Materials and Methods

Chemicals:

2,2'-(Ethylenedioxy)diethanethiol (EDDET), 1,4-dithioerythritol (DTT), pentaerythritol tetrakis(3-mercaptopropionate) (PETM), 1,3,5-triallyl-1,3,5-triazine-2,4,6(1H,3H,5H)-trione (TATATO), tri(ethylene glycol) divinyl ether (TEGDV), 1,7-octadiyne (OctDi), (+)-N,N'-diallyltartramide (DATA), 1-thioglycerol (TG), 1-octanethiol, N,N'-dimethyl acetamide (DMAc), (±)-1,3-butanediol (Budiol), di(propylene glycol)methyl ether acetate (DPMA), ethylene glycol (EG), diethylene glycol (DEG), triethylene glycol (TEG), tetraethylene glycol (TetEG), hexylene glycol, isopropanol, sodium dodecyl sulfate (SDS), 4-(2-hydroxyethoxy)phenyl-(2-hydroxy-2-propyl)ketone (IRGACURE 2959), 4,4'-azobis(4-cyanovaleric acid) (ACVA), cysteamine hydrochloride, 2-mercaptoethanol, mercaptosuccinic acid, sodium phosphate monobasic monohydrate, potassium phosphate dibasic, potassium phosphate monobasic, sodium acetate trihydrates, glacial acetic acid, sodium hydroxide pellet, glycine, citric acid, and D-(+)-trehalose dehydrate were obtained from Aldrich.

Proteins:

rProtein A-cys was obtained from Biomedal S.L (Seville, Spain). Polyclonal immuno γ-globulin IgG was obtained from Equitech-Bio Inc. (Kerrville, Tex., USA).

Membrane Preparation:

The crosslinker(s) and monomers (except thiol functionalized monomers, which were added 10 min prior to casting) were added with the photo-initiator (Irgacure 2959) to a solvent mixture, and the mixture was stirred long enough to dissolve all components. A pre-weighed 7"×8" porous support substrate sheet (non-woven polypropylene mesh) was placed on a polyethylene sheet, then ~15 g of the polymer solution was poured into the substrate sheet. The impregnated substrate was subsequently covered with another polyethylene sheet. The sheet was pressed gently in a circular motion by hand in order to remove excess solution and any entrapped air bubbles. The polymerization process was initiated by irradiating with UV light (~350 nm) the polymer solution/substrate sandwiched between polyethylene sheets in a closed chamber for 10 min. The resultant membrane was then removed from between the polyethylene sheets and subjected to extensive washing cycles that involved 20-30 minutes soaking periods in purified (RO) water (2-3 times) with agitation. The clean membranes were dried by hanging freely in the air at room temperature for ~16 hours.

Mass Gain, Wetting, and Permeability of Composite Membranes

The weight of the dried membrane was measured and used to calculate the mass gain. Wetting of the membrane was also determined by dispensing a 50 µL drop of distilled water on the membrane surface and measuring the time required for the drop to be absorbed within the membrane. To estimate membrane permeability, the flux of each membrane was determined using RO water (or acetate buffer pH 5) and a 7.7-cm diameter membrane sample, using 100 kPa applied pressure.

To estimate membrane permeability, the flux of RO water (or 132 mM acetate buffer pH 5) as mobile phase through each membrane was determined. Membranes were pre-soaked in testing fluid for at least 10 minutes prior to testing, flushed with ~300 mL of testing liquid, then the amount of the testing liquid that passes under 100 kPa applied pressure through a circular membrane coupon of 7.7 cm diameter (with actual 7.3 cm available diameter) was determined. The flux is expressed in the amount of liquid per surface area per time ($kg/m^2$ h).

Porous Structure Imaging:

To probe the gel structure and porosity, environmental scanning electron microscopy (ESEM) was used to image the membrane in the wet state. A small coupon (~7×5 mm) was wetted by soaking in distilled water for 10-15 minutes then examined using an ESEM instrument (FEI Quanta FEG 250 ESEM). The sample was placed on cooling stage to adjust the temperature to 5° C., and the image was examined at low pressure level (4.5-5.5 torr) and 50-55% relative humidity.

To probe the membrane structure in the dry state, Tescan Vega II LSU scanning electron microscope (SEM) (Tescan, Pa., USA) was used to image gold-coated membranes with voltage set to 10-20 kV.

Pore Size Measurements:

Membrane pore size (diameter) was measured using a CFP-1500-AE Capillary Flow Porometer (Porous Materials Inc., Ithaca, N.Y.), operated by CapWin software (V.6).

A small disc of membrane (2.5-cm diameter) was soaked in Galwick wetting liquid (Porous Materials Inc., surface tension=15.9 dynes/cm) for 10 min, then it was gently squeezed between two pre-wetted filter paper discs (Whatman 5-70 mm) to remove excess solution, and the thickness of the wetted membrane was determined using a micrometer. The membrane disc was then placed on a 2.5-cm stainless steel mesh support disc. The support disc loaded with the test membrane was placed in the designated holder, with the membrane facing up. The metal cover was then gently placed on the holder and the test was run within the pressure range of 0-200 psi.

Coupling Protocol for Conjugating Protein-A Ligand to Click Alkene Membrane:

To examine the feasibility of chemically binding biomolecules (with thiol functionality) to alkene membranes via a hydrothiolation click reaction, an engineered protein A ligand containing a cysteine residue was coupled to alkene membrane(s) (of different chemical formulas) and the bio-activity of the immobilized ligand was examined.

Protein A ligand lyophilized powder (r-Protein A-cys) was dissolved in PBS (20 mM sodium phosphate, 0.15 M NaCl, pH 7.4) to make a stock solution of 50 mg/mL. To make a coupling solution for each membrane, 0.4 mL of ligand stock solution was transferred into a small ziplock plastic bag (5×8 cm), to which 1.6 mL of 2 M phosphate buffer (pH 7.2) was added and then 50 µL of initiator (4,4'-azobis(4-cyanovaleric acid), ACVA) in DMAc (150 mg/mL) was added. The reaction solution was mixed well. The final reaction solution had a volume of ~2.0 mL, and contained about 20 mg of ligand, and about 7.5 mg of initiator.

Alternatively, ACVA was dissolved in the reaction buffer (2 M phosphate, pH 7.2) at a concentration of 5 mg/mL in order to avoid using DMAc. For low salt experiment, the initiator was dissolved in 0.5 M phosphate at a concentration of 7.5 mg/mL.

To the bag loaded with coupling reactants, a 4×7-cm membrane coupon (pre-wetted in water) was added. The bag was shaken for a minute, then irradiated with UV light (~365 nm) for 10 minutes. After irradiation was complete, the coupling solution was decanted, then 15-20 mL of washing buffer solution (0.1 M phosphate, pH 7.2) was added and the membrane was placed on the shaker for 10-15 minutes. The washing cycle was repeated three times, after which the membrane was either: (i) transferred into 8 mL of trehalose solution (10 wt. %), shaken for 10-15 minutes, and dried in an oven (50° C.) for 20-30 min; or (ii) stored in 0.1 M phosphate buffer.

For coupling in the presence of additives, ACVA was dissolved in 0.5 M potassium phosphate (pH 7.2) to make a solution having a concentration of 7.5 mg/mL. Protein A ligand was dissolved in 20 mM sodium phosphate buffer (pH 7.2) to make a 50 mg/mL stock solution. In each of three small bags (5×8 cm), 0.25 mL of ligand stock solution was mixed with 0.25 mL of initiator solution and 50 µL of an additive were added (cysteamine-HCl to reaction B bag, and 1-mercaptoethanol to reaction C bag).

After mixing the reaction solutions well, a 25-mm diameter membrane disc was placed in each bag and the reaction bags were shaken well, then irradiated by UV light for 10 minutes. The reaction solution was decanted, then membrane coupons were washed three times using 0.1 M sodium phosphate buffer (pH 7.2) and shaken for 10-15 minutes. The composite membrane coupons were stored in buffer (0.1 M sodium phosphate, pH 7.2) and tested for bio-affinity to IgG protein, as outlined previously.

Protein a Ligand Density on Composite Membranes:

To measure the Protein A ligand density on the coupled membrane, the amount of the uncoupled protein, which remained after the coupling reaction, was determined and subtracted from the total ligand amount to give the amount of the coupled ligand, then it was divided by the membrane volume (mL) to express density in mg ligand per mL of membrane.

To determine the Protein A amount in solution, a series of protein solutions in 0.1 M phosphate buffer (pH 7.2) were made, the absorbance at 280 nm was measured for each, and a calibration curve was constructed from which the slope was determined.

For selected membrane formulas, coupons of 4 cm×7 cm were cut and their thicknesses were measured, from which the volume was calculated. The coupling reaction was carried out as outlined previously, and 20 mg were loaded to each membrane coupling reaction, individually. When the UV reaction was complete, the reaction solution was collected in a tube, then 3-5 mL of 0.1 M phosphate buffer were added to the reaction bag and used to wash the membrane by shaking for 20-25 min, then the resulting solution was added to the collection tube.

The washing cycle was repeated two additional times, then the final solution absorbance was measured and the amount of uncoupled protein was calculated using the calibration curve slope. The coupled ligand amount was determined by taking the difference between the total reacted and uncoupled amounts.

Post-Polymerization Chemical Modification with Carboxylate Groups:

Additional membranes were synthesized and then modified by exploiting the click reaction to graft 1-mercaptosuccinic acid with alkene membranes in order to introduce carboxylate groups to the polymer backbone.

For example, a coupon having a diameter of 7.7 cm was cut from a membrane comprising a plurality of alkene functional groups and the flux was measured (initial flux). The coupon was then transferred into a plastic bag.

For these membranes, the grafting reaction was carried out in aqueous conditions. Mercaptosuccinic acid was dissolved in 6 mL deionized water, then 0.3 mL of ACVA initiator solution (150 mg/mL in DMAc) were added. The reaction solution was mixed well then added into the bag and mixed with the membrane coupon. This mixture was then irradiated in a UV chamber (approx. 350 nm) for 10 minutes.

After UV light exposure, the membrane coupons were removed from the bag and each coupon was rinsed twice with 20 mL of water, then twice with 20 mL of 0.1 M NaOH solution, and finally rinsed twice with 20 mL of water. The RO water flux and acetate buffer solution flux of the membrane were determined, then a small disc (25-mm diameter) was cut and used to determine cation exchange (CEX) IgG binding capacity.

Post-Polymerization Chemical Modification with Hydrophobic Ligands to Generate Hydrophobic Interaction Chromatography (HIC) Membranes Representative alkene-containing membranes were made as outlined above, then small coupons (4×7 cm each) were individually placed in small plastic zip-bags, each loaded with 3 mL of dimethylacetamide (DMAc) that contained 120 mg of 1-octanethiol and 10 mg of photoinitiator (ACVA). The reaction bags (with membrane coupons) were transferred into a closed UV chamber and irradiated with UV light for 10 minutes. Membranes were rinsed twice with 10 mL of DMAc, then rinsed once with 10 mL of 30% isopropanol in water, then rinsed twice with 10 mL of water. Membrane coupons were removed and dried in the oven (40° C.) for 10-15 minutes.

Binding Capacity Measurement:

Bio-Affinity IgG Binding Capacity

A 25-mm diameter membrane disc was placed in a 25-mm Natrix-Stainless Steel (SS) holder. 20 mL of binding buffer (20 mM sodium phosphate, 150 mM NaCl, pH 7.4) was passed through to equilibrate (~160-200 bed volume/min). In the binding step, 0.5 mg/mL polyclonal IgG in binding buffer was passed through at flow rate of 1 mL/min until the UV absorbance of the effluent exceeded 10% of the feeding solution, and then 10-15 mL of buffer was passed through to remove unbound protein at flow rate 2 mL/min. In the elution step, the bound IgG was eluted by passing 10-14 mL of elution buffer (0.1 M glycine-HCl, or 0.1 M sodium citrate, both at pH 3) at flow rate 2 mL/min.

Cation Exchange IgG Binding Capacity

A 25-mm membrane disc was placed in a 25-mm Natrix-SS holder and 20 mL of binding buffer (132 mM sodium acetate, pH 5.0) were passed through to achieve equilibration. Then protein solution (0.5 mg/mL human polyclonal IgG (Equitech-Bio Inc.) in binding buffer) was passed through until the UV absorbance of the effluent exceeded 10% of the feeding solution, and then 10-15 mL of buffer was passed through the cell to wash unbound protein. In the elution step, the bound IgG was eluted by passing 10 mL of elution buffer (132 mM sodium acetate, 1 M NaCl, pH 5.0; or 50 mM Tris, 0.5 M NaCl, pH 8.5).

Hydrophobic Interaction Mode IgG Binding Capacity

A 25-mm membrane disc was placed in a 25-mm Natrix-SS holder and 20 mL of binding buffer (50 mM sodium phosphate, 1 M ammonium sulfate, pH 6.5) was passed through to achieve equilibration. Then, a protein solution (0.5 mg/mL human polyclonal IgG (Equitech-Bio Inc.) in binding buffer) was passed through until the UV absorbance of the effluent exceeded 10% of the feeding solution. Subsequently, 15-20 mL of buffer was passed through the cell to wash unbound protein. In elution step, the bound IgG was eluted by passing 10 mL of elution buffer (50 mM sodium phosphate, pH 7.0).

Post-Polymerization Chemical Modification with Carboxylate Groups:

Selected membranes were modified by exploiting the click reaction to graft 1-mercaptosuccinic acid with alkene membranes in order to introduce carboxylate groups to the polymer backbone. For each membrane, a coupon having a diameter of 7.7 cm was cut and the flux was measured (initial flux). The coupon was then transferred into a plastic bag.

For modification in N,N'-dimethylacetamide (DMAc), a reaction solution was made by dissolving 0.3 g of 1-mercaptosuccinic acid in 6 mL of DMAc. Then, 0.3 mL of ACVA initiator solution (150 mg/mL in DMAc) were added to the thiol solution. Finally, the complete reaction solution was added to the reaction bag containing the membrane.

For aqueous reaction conditions, 6 mL deionized water were used instead of DMAc to dissolve mercaptosuccinic acid and 0.3 mL of ACVA initiator solution (150 mg/mL in DMAc) were added to it.

The bag was shaken well to ensure complete impregnation of the membrane with reaction solution, then it was irradiated by light (~365 nm) for 10 minutes, after which the reaction solution was discarded. 20 mL of water were added to the bag and the membrane was washed with agitation for 10 minutes. The wash solution was discarded and another 20 mL of water were added and the cycle was repeated. The membrane was washed twice more with 0.1 M NaOH (20 mL, 10 min. each). Finally, the membrane was washed twice more with water, and the flux of the membrane was determined (after flux).

Example 1—Formulation with TEGDV Co-Monomer

In certain embodiments, a hydrophilic co-monomer is included to help tune the membrane permeability.

In this membrane formulation class, 2,2'-(ethylenedioxy) diethanethiol (EDDET) monomer, and tri(ethylene glycol) divinyl ether (TEGDV), as co-monomer, were used as building monomers and 1,3,5-triallyl-1,3,5-triazine-2,4,6 (1H,3H,5H)-trione (TATATO) was used as a crosslinker. The solvent system included N,N'-dimethylacetamide (DMAc), (±)-1,3-butanediol (Budiol), di(propylene glycol)methyl ether acetate (DPMA), and water in variant amounts. 4-(2-Hydroxyethoxy)phenyl-(2-hydroxy-2-propyl)ketone (IRGACURE 2959) was used as photoinitiator to start the polymerization radical reaction.

Reaction mixtures based on these ingredients were formulated according to the tabulated data and all components were added and mixed well except the dithiol which was added 10-15 min prior to casting (to avoid any premature polymerization initiated by ambient light). Membranes were cast and polymerized as described previously. Mass gain and wetting time were determined and the initial flux of each membrane's coupon (7.7 cm in diameter) was measured using RO water.

The results (as shown in FIG. 1) show that it is possible to make membranes of various alkene/thiol ratio and versatile permeability, as indicated by water flux. The results also show that the solvent system may be used to help tune the membrane porosity and, as a result, the membrane permeability. For example, increasing 1,3-butanediol content while decreasing di(propylene glycol)methyl ether acetate (DPMA) content in the formula increased the membrane flux (Formulas CLK-EN-12 vs. CLK-EN-17 and CLK-EN-90 vs. CLK-EN-81). The results also show that replacing the crosslinker (TATATO) with the divinyl triethylene glycol extender has decreased membrane flux (Formulas CLK-EN-12 vs. CLK-EN-16).

While not wishing to be bound by any particular theory, 1,3-butanediol may be considered a non-solvent to the polymeric chain, and therefore tends to increase gel porosity during the polymerization step. As a result, permeability (expressed in water flux) increases. DPMA may play the same role.

Example 2—Formulation with TEGDV Co-Monomer—Effect of Initiator Concentration

In this example, the effects of the concentration of photoinitiator on the polymerization process and the resultant membrane properties were examined. Similar to the previous class, 2,2'-(ethylenedioxy)diethanethiol (EDDET) monomer, and tri(ethylene glycol) divinyl ether (TEGDV) co-monomer, and 1,3,5-triallyl-1,3,5-triazine-2,4,6(1H,3H,5H)-trione (TATATO) crosslinker were used. The solvent system included N,N'-dimethylacetamide (DMAc), butanediol (Budiol), di(propylene glycol)methyl ether acetate (DPMA), and water in varying quantities.

The amount of the 4-(2-hydroxyethoxy)phenyl-(2-hydroxy-2-propyl)ketone (IRGACURE 2959) photoinitiator was varied, according to FIG. 2 for two sets of polymerization reactions, one at 10 minutes polymerization time (CLK-EN-27 and CLK-EN-45) and the other (CLK-EN-137 to 140) at 6 minutes polymerization time. The shorter polymerization time was examined to allow a better discrimination, based on initiator amount, of the resultant membrane properties because the hydrothiolation click reaction is a fast reaction.

The results, as shown in FIG. 2, suggest that initiator amount has an effect on membrane permeability. The flux tends to decrease as the initiator amount increases. This effect demonstrated itself at both 10 and 6 minutes polymerization time. While not wishing to be bound by any particular theory, more initiator means that the polymerization proceeds to a higher rate of conversion; the likely result is a denser polymeric network.

Example 3—Formulation with TEGDV and DATA as Co-Monomers

In this example, another hydrophilic co-monomer (N,N'-diallyltartramide (DATA)) was examined. While not wishing to be bound by any particular theory, the two hydroxyl groups in this molecule increase the amphiphilic nature of the polymer, which may enhance phase separation as the polymer chains grow, thereby improving the porosity of the final gel.

In this membrane formulation class, 2,2'-(ethylenedioxy)diethanethiol (EDDET) monomer and tri(ethylene glycol) divinyl ether (TEGDV) and (+)-N,N'-diallyltartramide (DATA) co-monomers, were used as building monomers with 1,3,5-triallyl-1,3,5-triazine-2,4,6(1H,3H,5H)-trione (TATATO) as a crosslinker.

The solvent system included N,N'-dimethylacetamide (DMAc), (±)-1,3-butane diol (budiol), di(propylene glycol) methyl ether acetate (DPMA), and water in varying amounts. 4-(2-Hydroxyethoxy)phenyl-(2-hydroxy-2-propyl)ketone (IRGACURE 2959) was used as photoinitiator to start the polymerization reaction.

The reaction components were mixed well together, except the dithiol which was added 10-15 min prior to casting. The membranes were cast and polymerized as described previously. Mass gain and wetting time were determined, then the initial flux of each membrane coupon (7.7 cm in diameter) was measured using RO water.

The results for this example demonstrate again the effect of the solvent system on the membrane permeability. As seen when comparing formula CLK-EN-99 with CLK-EN-104 (FIG. 3), reducing the amount of 1,3-butandiol and increasing the amount of N,N'-dimethylacetamide (DMAc) result in a remarkable reduction of permeability (water flux decreased from about 10,000 to about 1700 kg/m$^2$ h).

In general, 1,3-butanediol and water are considered non-solvents or poor solvents to the polymeric chain; therefore porosity of membranes formed in these solvents is increased. On the contrary, DMAc is considered a good solvent that helps solvate the polymeric chain as it forms; as a result, porosity and permeability are reduced.

Example 4—Formulation with DATA as Co-Monomer

In this example, the use of N,N'-diallyltartramide (DATA) as the sole co-monomer was examined. DATA molecules have internal amide bonds (which TEGDV molecules do not have); these may add some mechanical strength to the resulting membrane.

In this membrane formulation class, 2,2'-(ethylenedioxy) diethanethiol (EDDET) monomer, (+)-N,N'-diallyltartramide (DATA) as co-monomer, and 1,3,5-triallyl-1,3,5-triazine-2,4,6(1H,3H,5H)-trione (TATATO) as a crosslinker were used to make the membranes. The solvent system included N,N'-dimethylacetamide (DMAc), (±)-1,3-butanediol (Budiol), di(propylene glycol)methyl ether acetate (DPMA), and water in varying amounts. 4-(2-Hydroxyethoxy)phenyl-(2-hydroxy-2-propyl)ketone (IRGACURE 2959) was used as the photoinitiator.

The reaction components (FIG. 4) were mixed well together, except the dithiol which was added 10-15 min prior to casting. The membranes were cast and polymerized as described previously. Mass gain and wetting time of the dried membranes were determined, then the initial flux of each membrane's coupon (7.7 cm in diameter) was measured using R.O. water.

The results (FIG. 4) show that increasing DATA content (from 3.3% to 7.6%), with concomitant decrease in the crosslinker content (from 16.3% to 9.9%), reduced the membrane flux.

Reducing dithiol (EDDET) content in this system lead to an increase in the membrane flux (CLK-EN-149 to −151). While not wishing to be bound by any particular theory, it is possible that higher dithiol content helps in connecting smaller growing polymeric chains, resulting in denser gel with higher mass gain and lower flux.

Figure 6:
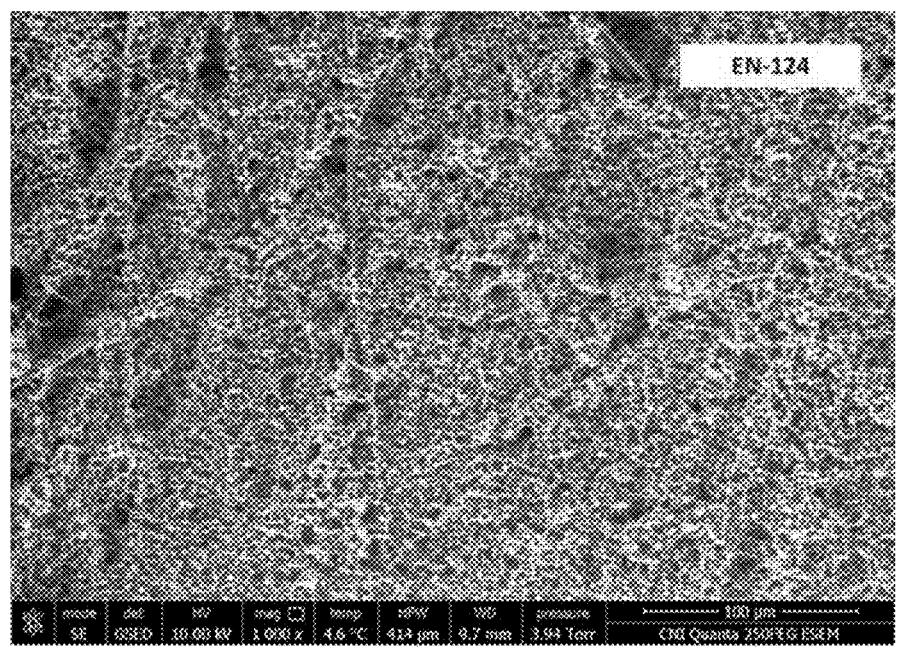
FIG. 6 depicts an ESEM image of a composite membrane (EN-124) formulated with DATA as co-monomer; the alkene-to-thiol ratio in the polymerization mixture for making this membrane was 1.27.

These membranes were examined by environmental scanning electron microscopy (ESEM), which showed porosity of the gel (FIG. 6).

Example 5—Formulation with Dialkyne Crosslinker

In this example, dialkyne molecule (1,7-octadiyne) was examined as an additional crosslinker that can boost the unsaturated carbon-carbon bond population within the formulated membrane. This can be beneficial as it increases the possibility of engrafting the gel with thiol functional (bio) molecules.

In this membrane formulation class, 2,2'-(ethylenedioxy) diethanethiol (EDDET) monomer and tri(ethylene glycol) divinyl ether (TEGDV) co-monomer were used as building monomers, while 1,3,5-triallyl-1,3,5-triazine-2,4,6(1H,3H, 5H)-trione (TATATO) and 1,7-octadiyne (OctDi) were used as crosslinkers. The solvent system included N,N'-dimethylacetamide (DMAc), (±)-1,3-butanediol (Budiol), di(propylene glycol)methyl ether acetate (DPMA), and water, all in varying amounts. 4-(2-Hydroxyethoxy)phenyl-(2-hydroxy-2-propyl)ketone (IRGACURE 2959) was used as photoinitiator.

The reaction components (FIG. 7), except the dithiol (EDDET), were mixed until all dissolved. Then, EDDET was added 10-15 min prior to casting. Membranes were cast and polymerized as described previously. Mass gain, wetting time, and initial flux of each membrane coupon (7.7 cm in diameter—using R.O. water) were determined.

Figure 8A:
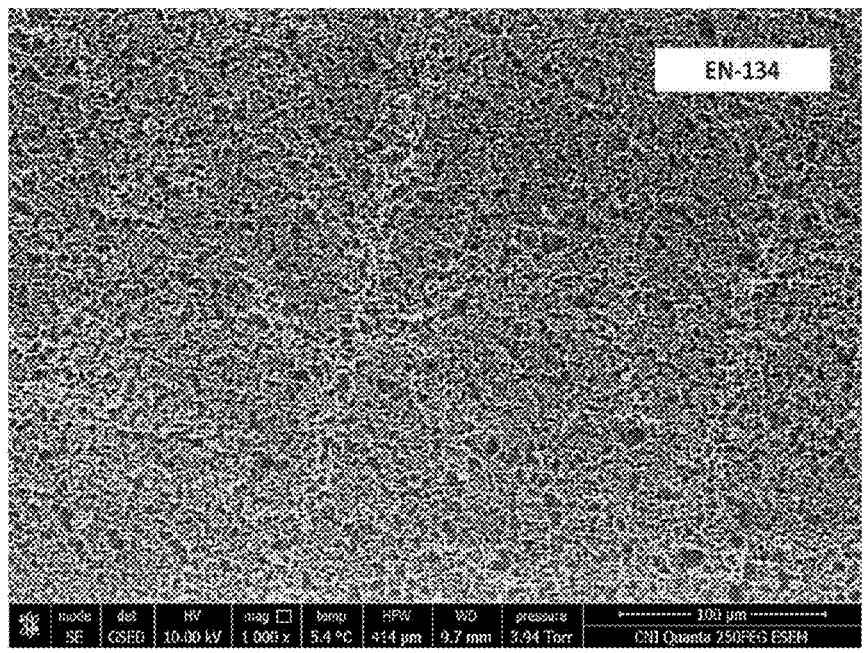
FIG. 8A depicts an ESEM image of a composite membrane prepared with octadiyne as an additional crosslinker prepared with an alkene-to-thiol ratio of 1.074 (EN-134).
Figure 8B:
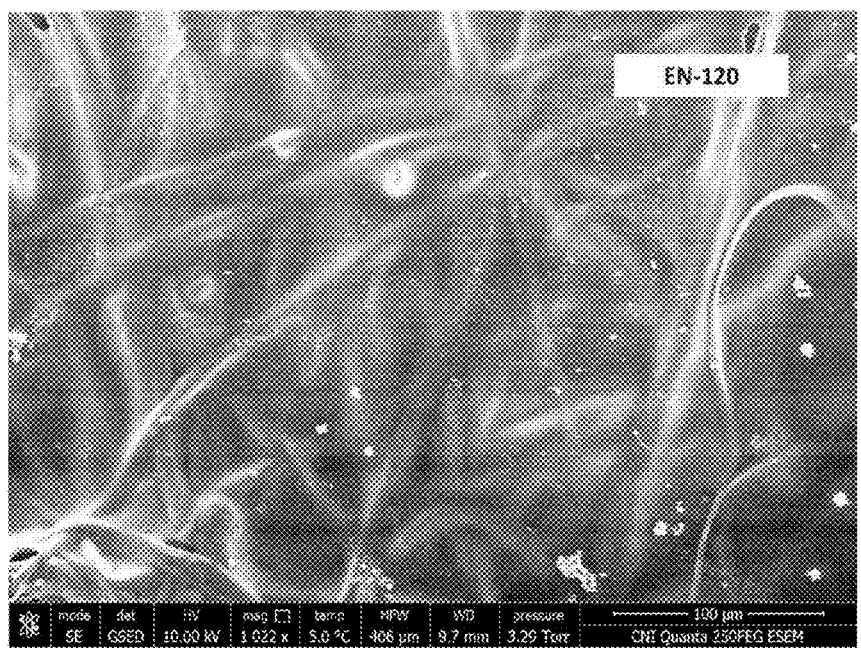
FIG. 8B depicts an ESEM image of a composite membrane prepared with octadiyne as an additional crosslinker prepared with an alkene-to-thiol ratio of 1.18 (EN-120).

Results shown in FIG. 7 demonstrate that it is possible to formulate membranes with octadiyne as a co-crosslinker. Decreasing the amount of crosslinkers (TATATO & OctDi) results in a composite membrane having lower permeability. ESEM shows the porous structure of these membranes (FIG. 8).

Example 6—Post-Polymerization Grafting of Alkene/yne Membrane with Carboxylate Groups by Hydrothiolation Carboxylate groups are hydrophilic in nature and known to increase gel swelling due to the strong hydration of the ionized form (e.g., polymethacrylates). Increasing the carboxylate group content in the gel increases the gel swelling, which in turn decreases the flux. On the other hand, carboxylic acid groups (i.e., acid form) are considered relatively hydrophobic; a gel having carboxylic acid moieties in their non-ionized form does not swell as much, and the flux increases. This phenomenon is known as hydrogel pH sensitivity.

To demonstrate the capability of grafting a click alkene polymer with new functionality by using a post-polymerization click reaction, alkene/yne membranes having high water flux were made (FIG. 9). These membranes were subject to click hydrothiolation functionalization with a thiol-acid molecule. The permeability of the modified membrane, expressed in flux, was determined and compared with the initial flux prior to the grafting reaction.

The post-polymerization grafting click reaction was carried out in DMAc or water. The flux of each modified membrane was measured using RO water. To probe the pH sensitivity of the modified membranes, acetate buffer (132 mM acetate, pH 5) was used.

Figure 10:
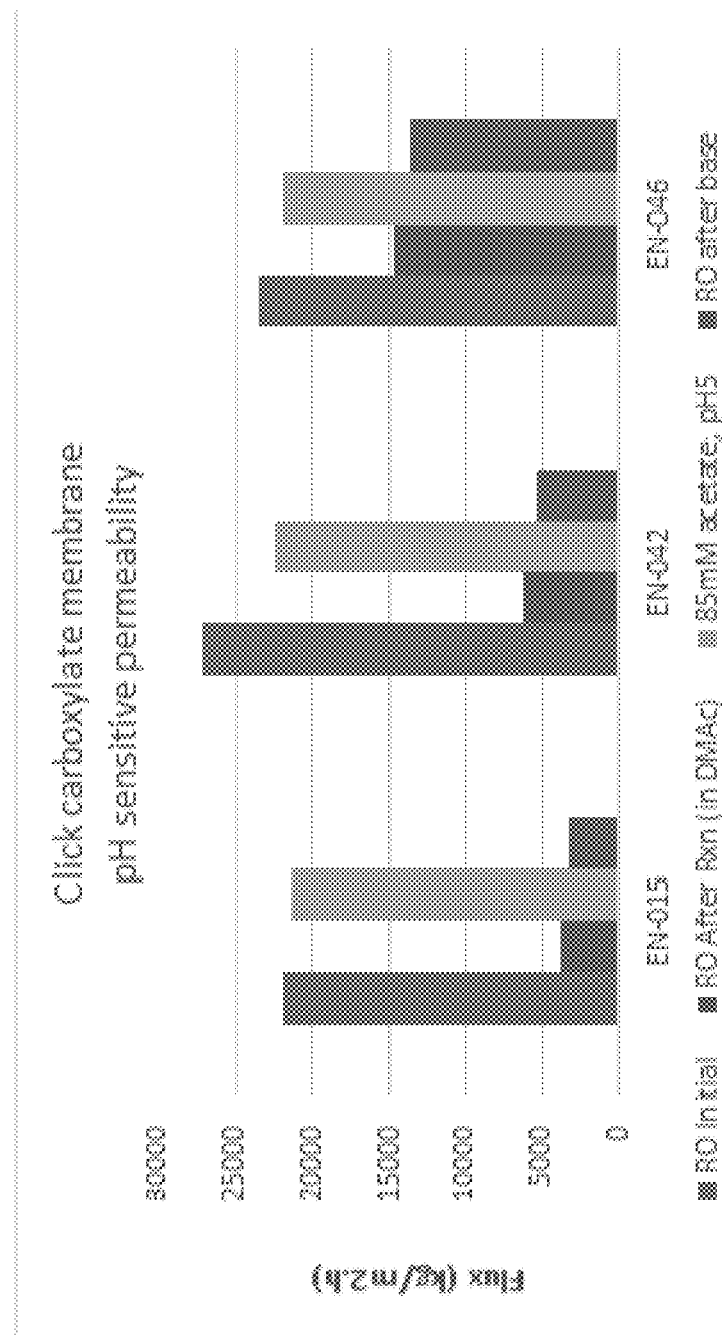
FIG. 10 depicts a graphical representation of the water flux of various composite membranes of the invention before being grafted with carboxylate moieties (left bar) and after being grafted with carboxylate moieties (second left bar). Upon exposure to pH 5, the flux increases (second right bar). Upon exposure to 0.1 M NaOH, the flux decreases again (right bar).

The flux of the modified membranes decreased as compared to their flux before grafting (Table 1). When the flux was determined using acetate buffer at pH 5, the flux increased because the carboxylate group was converted into the hydrophobic form (carboxylic acid), which decreased the gel swelling. Furthermore, when the membrane was flushed with 0.1 M NaOH solution, the R.O. flux dropped which confirms the membrane pH sensitivity because of the deprotonation of the carboxylic acid groups to form carboxylate groups at basic pHs. See also FIG. 10.

TABLE 1

Membrane flux (kg/m²h) in solvents with varying pH

| Formula | Initial RO Flux | RO Flux After Grafting | pH 5 Acetate RO Flux After Grafting | NaOH RO Flux After Grafting | Alkene/thiol ratio |
|---|---|---|---|---|---|
| CLK-EN-015 | 21917 | 3806 | 21333 | 3318 | 1.35 |
| CLK-EN-042 | 27143 | 6138 | 22399 | 5405 | 1.44 |
| CLK-EN-046 | 23509 | 14676 | 21896 | 13650 | 1.44 |

Figure 11:
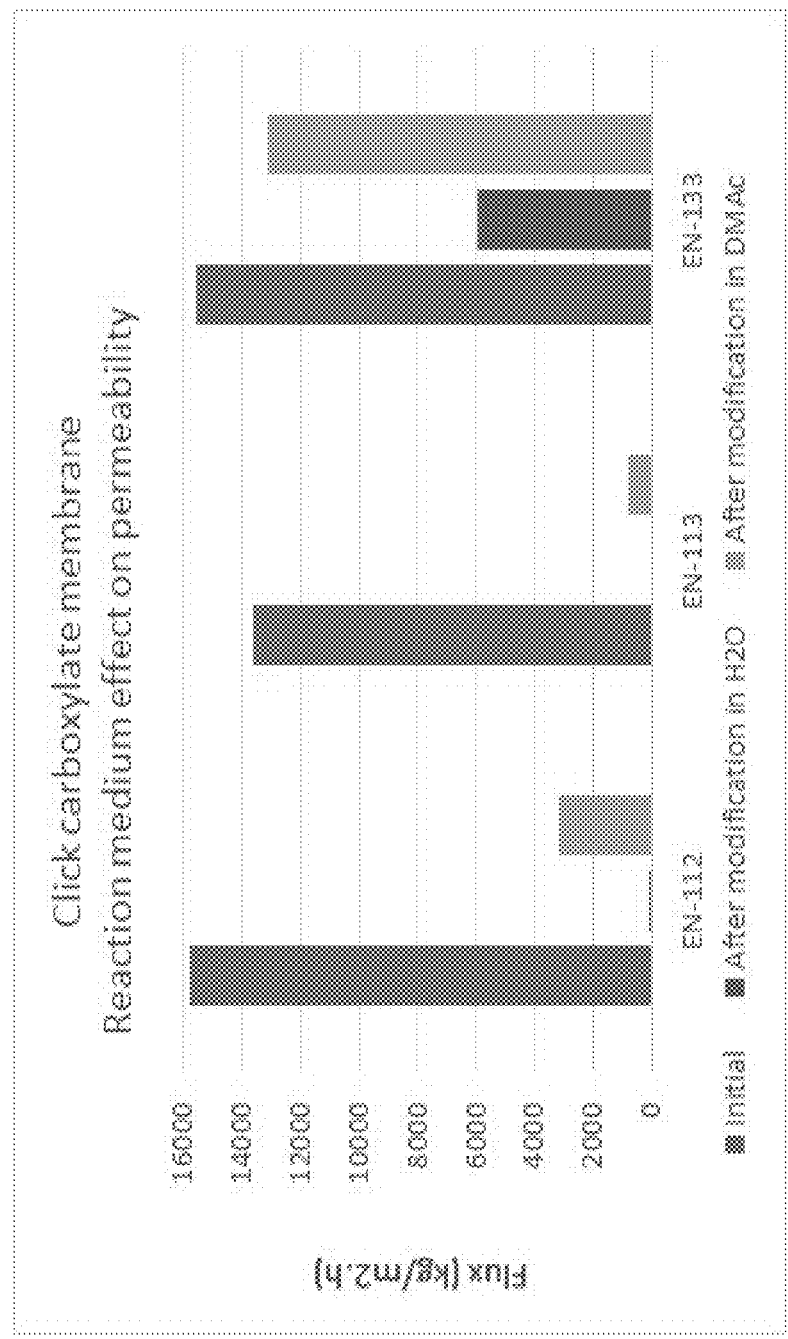
FIG. 11 depicts a graphical representation of the water flux of various composite membranes of the invention before being grafted with carboxylate moieties (left bar), after being grafted in water with carboxylate moieties (center bar), and after being grafted in DMAc with carboxylate moieties (right bar).

To examine the effect that the reaction medium has on the properties of the modified membrane, the grafting hydrothiolation reaction was carried out on a membrane in DMAc and separately in water, and the flux of the modified membranes in different media was evaluated. As shown below (Table 2), membranes grafted in water have lower flux than counterpart membranes that were modified in DMAc. This coincides with general understanding that the hydrothiolation reaction is more reactive in polar solvents, and in aqueous media in particular. See also FIG. 11.

TABLE 2

Effect of solvent during grafting reaction on membrane flux (kg/m²h)

| Formula | Initial RO Flux | RO Flux after modification in H₂O | RO Flux after modification in DMAc | Alkene/thiol ratio |
|---|---|---|---|---|
| EN-112 | 15758 | 92 | 3141 | 1.23 |
| EN-113 | 13612 | 0 | 833 | 1.21 |
| EN-133 | 15531 | 5980 | 13103 | 1.08 |

Example 7—Post-Polymerization Grafting of Alkene/yne Membrane with Protein A by Hydrothiolation To demonstrate that the click alkene membranes may be grafted with a biological ligand, protein A having with cysteine terminal functionality (rProtein A-cys) was coupled to selected click alkene membranes as described above. The binding capacity of the membrane with grafted protein A moieties was determined by examining its bio-affinity for IgG protein, following the binding/elution protocol, as outlined above.

Binding capacity results (Table 3) demonstrate that the protein A-modified membranes are capable of binding IgG. This would not be possible if the ligand was not coupled to the gel membrane or was inactive. The elution solution for EN-151 was citrate buffer solution (0.1 M, pH 3), while glycine hydrochloride buffer solution (0.1 M, pH 3) was used in the elution step for EN-134 and EN-152.

It is interesting to note that the coupling reaction took place even when the alkene-to-thiol ratio was less than 1, which suggests that the original polymerization reaction did not consume all alkene groups. Because polymeric chain growth can impede chain mobility during the final stages of the polymerization reaction, this is not unexpected. So, it is possible that any excess thiol is coupling to the residual alkene groups in the polymer.

The results also show that the alkene-to-thiol ratio is not the sole factor in controlling the coupling reaction. For example, a higher ratio did not result in higher coupling and concomitant bioactivity. Other factors such as porosity, surface area, and surface hydrophilic/hydrophobic nature, contribute to the accessibility of the alkene groups, thereby affecting the coupling reaction.

TABLE 3

IgG binding capacity of engrafted click-protein A membrane

| Formula | Alkene/thiol ratio | RO Flux (kg/m²h) | IgG Binding Capacity$_{10\%B.T}$ (mg/mL) |
|---|---|---|---|
| CLK-EN-016 | 1.363 | 2189 | 1.4 |
| CLK-EN-027 | 1.238 | 1468 | 1.3 |
| CLK-EN-134 | 1.074 | 6979 | 3.7 |
| CLK-EN-118 | 1.278 | 11509 | 1.6 |
| CLK-EN-124 | 1.273 | 14895 | 2.8 |
| CLK-EN-143 | 0.963 | 9007 | 4.9 |
| CLK-EN-149 | 0.963 | 3804 | 5.0 |
| CLK-EN-150 | 1.015 | 6700 | 5.5 |
| CLK-EN-151 | 1.052 | 7808 | 6.2 |
| CLK-EN-152 | 0.963 | 7674 | 5.6 |

Example 8—Effect of Grafting Reaction Time and Amount of Ligand on Properties of Modified Membranes In order to use the radical hydrothiolization (thiol-ene) reaction to graft protein A to alkene membranes, the reaction must be initiated by UV radiation. Therefore, it was necessary to investigate the effects of this exposure on the grafted ligand bioactivity.

One membrane formula was subject to protein A coupling experiments during which the light dose (at 365 nm), gauged by exposure time, was varied and the effect on bioactivity (as reflected by binding capacity) was examined (Table 4).

The results suggest that varying the exposure time from 10 to 20 minutes does not affect the binding capacity of the final modified membrane, regardless of the ligand amount or concentration in the reaction solution. The results also show that increasing the amount of protein improved bioactivity.

TABLE 4

Light and ligand amount effects on coupling reaction

| Experiment | Reaction Volume (mL) | Conc. (mg/mL) | Total ligand amount (mg) | Exposure time (min) | Binding Capacity (mg/mL) |
|---|---|---|---|---|---|
| A | 1 | 10 | 10 | 10 | 0.7 |
| B | 1 | 10 | 10 | 20 | 0.7 |
| C | 2 | 5 | 10 | 10 | 0.9 |
| D | 2 | 5 | 10 | 20 | 0.8 |
| E | 2 | 10 | 20 | 10 | 1.3 |
| F | 2 | 10 | 20 | 20 | 1.3 |

Example 9—Effect of the Presence of Competing Additives on Properties of Modified Membranes To demonstrate that a hydrothiolation reaction is responsible for attaching the cys-protein A ligand to the alkene membrane, the coupling reaction was carried out on small 25-mm diameter discs of the same membrane (CLK-EN-143) in the presence and absence of thiol-functionalized molecules, which can compete with the ligand for the available alkene groups and, therefore, limit the extent of the ligand coupling reaction. Indeed, the ligand coupling reaction in the presence of competing thiol molecules resulted in membranes having reduced bioactivity, compared to the modified membrane formed in the absence of thiol-functionalized additives. FIG. 12.

Example 10—Formulation with DATA as Co-Monomer

In this example, the use of N,N'-diallyltartramide (DATA) as the sole co-monomer was examined. DATA molecules have internal amide bonds (which TEGDV molecules do not have); these may add some mechanical strength to the resulting membrane.

In this membrane formulation class, 2,2'-(ethylenedioxy) diethanethiol (EDDET) monomer, (+)-N,N'-diallyltartramide (DATA) as co-monomer, and 1,3,5-triallyl-1,3,5-triazine-2,4,6(1H,3H,5H)-trione (TATATO) as a crosslinker were used to make the membranes. The solvent system included N,N'-dimethylacetamide (DMAc), (±)-1,3-butanediol (Budiol), di(propylene glycol)methyl ether acetate (DPMA), and water in varying amounts, or N,N'-dimethylacetamide (DMAc), (±)-1,3-butanediol (Budiol), di(ethylene glycol), tri(ethylene glycol), and water in varying amounts. 4-(2-Hydroxyethoxy)phenyl-(2-hydroxy-2-propyl)ketone (IRGACURE 2959) was used as the photoinitiator.

The reaction components (FIG. 4B and FIG. 13) were mixed well together, except the dithiol which was added 10-15 min prior to casting. The membranes were cast and polymerized as described previously. Mass gain and wetting time of the dried membranes were determined, then the initial flux of each membrane's coupon (7.7 cm in diameter) was measured using RO water.

The results (FIG. 4B and FIG. 13) show that it is possible to feed DATA co-monomer over a wide range by using different solvent systems to obtain a wide range of membrane permeabilities, as indicated by membrane water flux measurements. When these membranes were grafted with Protein A ligand, they showed a corresponding range of IgG binding capacities (see post polymerization grafting with Protein A section).

Figure 14:
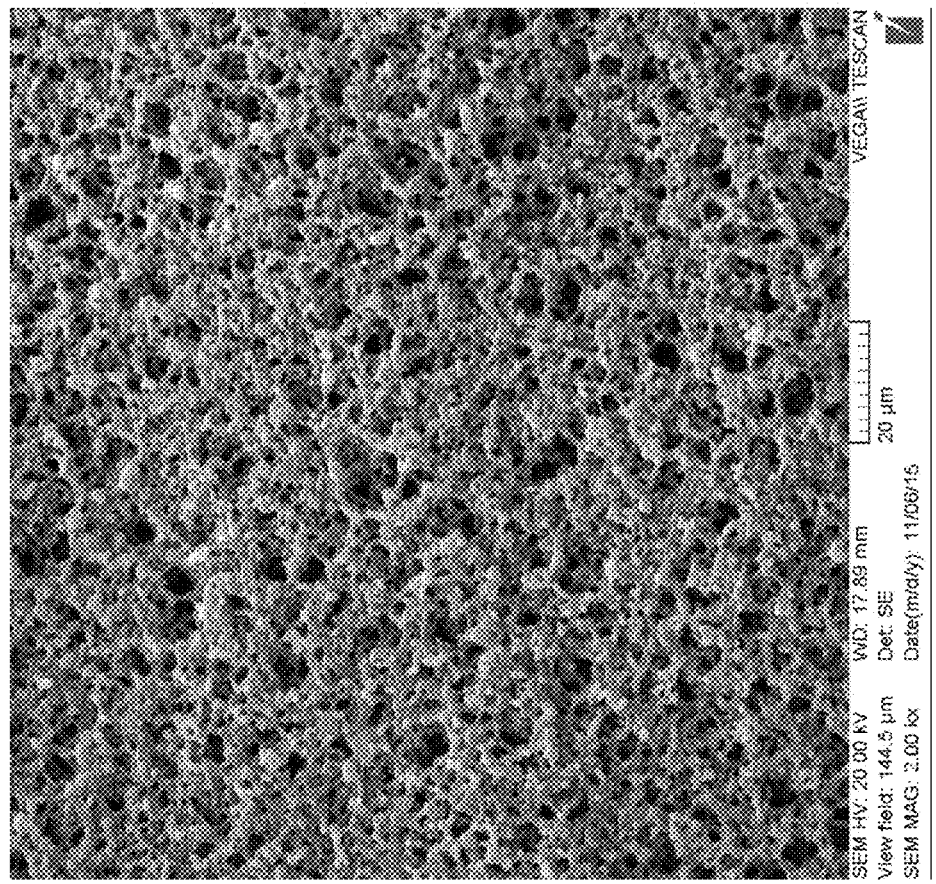
FIG. 14 depicts an SEM image of CLK-EN-298 membrane.

These membranes were examined by scanning electron microscopy (SEM), which revealed uniform, highly interconnected porous networks (FIG. 14).

Example 11—Formulation with Tetrathiol Molecule as a Co-Crosslinker

In certain embodiments, pentaerythritol tetrakis(3-mercaptopropionate) (PETM) was used as an additional crosslinker in order to modify the resulting membrane structure and permeability.

In this membrane formulation series, 2,2'-(ethylenedioxy) diethanethiol (EDDET) monomer, and (+)-N,N'-diallyltartramide (DATA) co-monomers, were used as monomers and 1,3,5-triallyl-1,3,5-triazine-2,4,6(1H,3H,5H)-trione (TATATO) and pentaerythritol tetrakis(3-mercaptopropionate) (PETM) were used as an additional crosslinker. The solvent system included N,N'-dimethyl acetamide (DMAc), (±)-1,3-butanediol (Budiol), hexylene glycol, ethylene glycol (EG), tetra(ethylene glycol) (TetEG) and water in variant amounts. 4-(2-Hydroxyethoxy)phenyl-(2-hydroxy-2-propyl)ketone (IRGACURE 2959) was used as photoinitiator to start the polymerization radical reaction.

Reaction mixtures based on these ingredients were formulated (FIG. 8) and all components were added and mixed well except the dithiol which was added 10-15 min prior to casting (to avoid any premature polymerization initiated by ambient light). Membranes were casted and polymerized as described previously. Mass gain and wetting time were determined and the initial flux of each membrane's coupon (7.7 cm in diameter) was measured using RO water.

Figure 16:
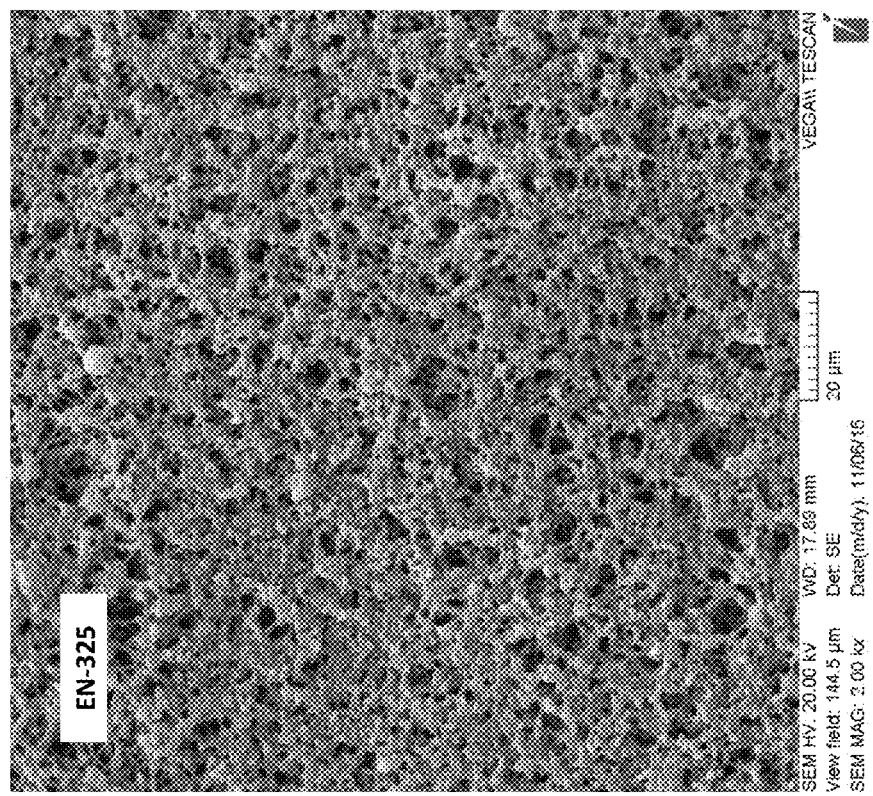
FIG. 16 depicts an SEM image of EN-325 membrane made using a tetrathiol (PETM) cross-linker.

The results (as shown in FIG. 15) show that it is possible to use multi-arm thiol (PETM) as a second crosslinker to produce membranes of various alkene/thiol ratio with variable permeability, as indicated by water flux. It is possible to increase the permeability by increasing the overall crosslinkers content in the gel, as demonstrated in Table 5. SEM shows the porous structure of a representative membrane formulation (FIG. 16).

varying amounts. 4-(2-Hydroxyethoxy)phenyl-(2-hydroxy-2-propyl)ketone (IRGACURE 2959) was used as photoinitiator.

The reaction components (FIG. 17), except the dithiol (EDDET), were mixed in the solvent mixture until completely dissolved. Then, EDDET was added 10-15 min prior to casting. Membranes were casted and polymerized as described previously. Mass gain, wetting time, and initial flux of each membrane coupon (7.7 cm in diameter—using R.O. water) were determined.

Figure 18:
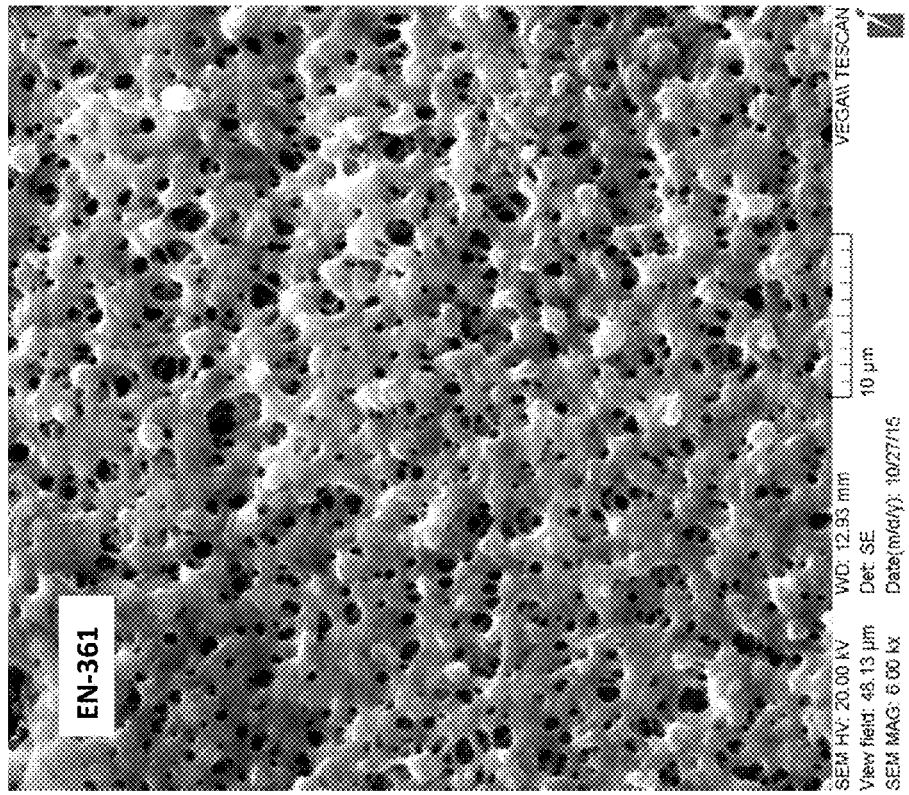
FIG. 18 depicts an SEM image of the CLK-EN-361 membrane.

Results shown in FIG. 17 demonstrate that it is possible to formulate membranes with octadiyne as a co-crosslinker that vary widely in their permeability. Scanning electron microscopy (SEM) image of a representative membrane (CLK-EN-361) shows a uniform, interconnected porous structure containing small pores (FIG. 18).

TABLE 5

Effect of PETM crosslinker on membrane permeability

| Formula | mole % (mol %) | | | | Total crosslinker mole % | RO Flux |
|---|---|---|---|---|---|---|
| | EDDET | PETM | TATATO | DATA | PETM + TATATO | (kg/m$^2$h) |
| CLK-EN-314 | 45.62 | 7.26 | 23.94 | 22.78 | 31.2 | 6781 |
| CLK-EN-317 | 45.22 | 7.07 | 26.17 | 21.14 | 33.24 | 7995 |
| CLK-EN-323 | 40.68 | 12.16 | 25.50 | 21.42 | 37.66 | 14788 |
| CLK-EN-325 | 40.81 | 12.28 | 25.75 | 20.83 | 38.02 | 11812 |

Example 12—Additional Formulations with Dialkyne Crosslinker

In this set of additional examples, a dialkyne molecule (1,7-octadiyne) was included in the formula as an additional crosslinker to increase the unsaturated carbon-carbon bond population within the polymerized membrane.

In this membrane formulation class, 2,2'-(ethylenedioxy)diethanethiol (EDDET) monomer and (+)-N,N'-diallyltartramide (DATA) co-monomers, were used as monomers and 1,3,5-triallyl-1,3,5-triazine-2,4,6(1H,3H,5H)-trione (TATATO) and 1,7-octadiyne (OctDi) were used as crosslinkers. The solvent system included N,N'-dimethylacetamide (DMAc), sodium dodecyl sulfate (SDS), ethylene glycol (EG), tetra(ethylene glycol) (TetEG), and water, all in Example 13—Cation Exchange IgG Binding Using Membranes Functionalized with Carboxylate Groups Carboxylate groups are hydrophilic in nature and known to increase polymer swelling due to the strong hydration of the ionized form (e.g., polymethacrylates). Increasing the carboxylate group content in the porous polymer increases the swelling, which in turn decreases the flux. See Example 6.

The cation exchange binding capacity for protein IgG (which has net positive charge at pH 5) for each grafted membrane was examined to provide additional support for the incorporation of the charged cation exchange ligands in the membrane. The membranes' dynamic binding capacity for IgG increases with increasing alkene/thiol ratio. See Table 6.

TABLE 6

Effect of attaching carboxylate groups on membrane flux (kg/m$^2$h) and IgG binding capacity

| Formula | Initial RO Flux (kg/m$^2$h) | RO Flux After Grafting (kg/m$^2$h) | Acetate pH 5 Flux After Grafting (kg/m$^2$h) | CEX IgG Binding Capacity$_{10\%B.T}$ (mg/mL) | Alkene/thiol ratio |
|---|---|---|---|---|---|
| CLK-EN-237 | 15432 | 1725 | 13353 | 19.5 | 1.101 |
| CLK-EN-227 | 13664 | 705 | 11848 | 22.2 | 1.101 |
| CLK-EN-224 | 17189 | 773 | 14375 | 28.1 | 1.129 |
| CLK-EN-287 | 6972 | 20 | 5198 | 37.5 | 1.135 |
| CLK-EN-235 | 12243 | 34 | 10041 | 37.3 | 1.142 |
| CLK-EN-291 | 10172 | 24 | 7539 | 37.9 | 1.159 |
| CLK-EN-298 | 6918 | 0 | 5533 | 44.2 | 1.159 |
| CLK-EN-301 | 13841 | 15 | 10684 | 54.7 | 1.211 |
| CLK-EN-256 | 16246 | 7 | 15777 | 50.6 | 1.222 |

Example 14—Post-Polymerization Grafting of Alkene/yne Membrane (Made with DATA Co-Monomer) with Protein A by Hydrothiolation To demonstrate that the click alkene membranes may be grafted with a biological ligand, an engineered Protein A ligand containing a C-terminal cysteine residue (rProtein A-cys) was coupled to selected click alkene membranes that were made as described above. The IgG binding capacity of the membrane with grafted Protein A ligand was determined, as outlined above.

IgG binding capacity results (Table 7) of the membrane with higher DATA content (i.e., >8 wt. % in the polymerization mixture) demonstrate that the Protein A-modified membranes are capable of binding more IgG than membranes having a lower relative concentration of DATA monomer (i.e., <8 wt. % in the polymerization mixture).

The results also suggest that the alkene-to-thiol ratio is not the only variable correlated to membrane IgG binding capacity performance. Other factors such as porosity, surface area, and surface hydrophilic/hydrophobic nature, likely also play important roles, as they contribute to the accessibility of the alkene groups, thereby affecting the Protein A ligand coupling reaction.

TABLE 7

IgG binding capacity of Protein A-grafted membranes (with increased DATA co-monomer in reaction solution)

| Formula | wt. % DATA | Alkene/thiol ratio | RO Flux (kg/m²h) | IgG Binding Capacity$_{10\%B.T}$ (mg/mL) | Ligand density on ProA membrane (mg/mL) |
|---|---|---|---|---|---|
| CLK-EN-301 | 8.26 | 1.211 | 13841 | 9.6 | 6.9 |
| CLK-EN-227 | 8.47 | 1.101 | 13664 | 7.3 | 5.9 |
| CLK-EN-237 | 8.48 | 1.101 | 15432 | 8.3 | |
| CLK-EN-256 | 8.52 | 1.222 | 16246 | 9.2 | 6.4 |
| CLK-EN-298 | 8.52 | 1.159 | 6918 | 10 | 5.7 |
| CLK-EN-291 | 8.54 | 1.159 | 10172 | 9.8 | 7.0 |
| CLK-EN-235 | 8.67 | 1.142 | 12243 | 10.8 | |
| CLK-EN-287 | 8.96 | 1.135 | 6972 | 10.2 | |
| CLK-EN-224 | 9.10 | 1.129 | 17189 | 6 | 5.3 |

Example 15—Post-Polymerization Grafting of Alkene/yne Membrane (Made with PETM Co-Crosslinker) with Protein A by Hydrothiolation In this class of membrane, the tetrathiol crosslinker PETM was used as an additional crosslinker to provide another tool to tune the degree of crosslinking and permeability of the membranes. The presence and surface density of post-polymerization alkene functional groups were probed by first grafting Protein A ligand to these membranes using the radical hydrothiolation (thiol-ene) reaction. Then the IgG binding capacity of the Protein A-grafted membranes was assessed as described previously.

As shown below (Table 8), the results suggest that membranes made with this co-crosslinker possess residual alkene groups that are functional and accessible for the rProtein A-cys hydrothiolation (thiol-ene) reaction on the membrane surface.

TABLE 8

IgG binding capacity of Protein A-grafted membranes (made with PETM co-crosslinker)

| Formula | Alkene/thiol ratio | RO Flux (kg/m²h) | IgG Binding Capacity$_{10\%B.T}$ (mg/mL) |
|---|---|---|---|
| CLK-EN-314 | 1.128 | 6781 | 10.3 |
| CLK-EN-317 | 1.176 | 7995 | 10.7 |
| CLK-EN-323 | 1.183 | 14788 | 8.9 |
| CLK-EN-325 | 1.174 | 11812 | 11.8 |

Example 16—Post-Polymerization Grafting of Alkene/yne Membrane with Hydrophobic Ligand to Generate Hydrophobic Interaction Chromatography (HIC) Media A hydrophobic thiol-terminated molecule was grafted to membranes containing residual alkene functional groups using a photoinitiated click (thiol-ene) hydrothiolation reaction. Three membranes (EN-224, EN-291, and EN-301) were prepared (as outlined previously in the experimental methods section) for use in subsequent grafting reactions, namely to introduce 1-octanethiol onto the membrane, as described in the general methods section.

Attachment of the hydrophobic thiol to the membranes was expected to significantly decrease the surface hydrophilicity of the grafted membrane versus the ungrafted membrane. Indeed, the wetting time consistently increased post-grafting for all of the membrane formulations tested (Table 9).

The hydrophobic ligand-modified membranes were anticipated to serve as effective hydrophobic interaction chromatography (HIC) media, binding IgG at high salt concentrations. This phenomenon constitutes the basis of hydrophobic interaction chromatography, a well-known technique utilized in bio-separation process for biologicals purification.

Results (Table 9) demonstrate that the modified membrane indeed can bind protein in high salt conditions.

TABLE 9

Properties of alkene/yne membranes grafted with hydrophobic ligand

| Formula | Alkene/thiol ratio | Wetting Time Before | Wetting Time After | HIC Binding Capacity$_{10BT\%}$ (mg/ml) |
|---|---|---|---|---|
| CLK-EN-224 | 1.129 | 1 Sec | 6 Sec | 10.6 |
| CLK-EN-291 | 1.159 | 1 Sec | 20 Sec | 12.4 |
| CLK-EN-301 | 1.211 | 1 sec | 20 sec | 10.8 |

Example 17—One-Step Polymerization Reaction for Making Functionalized HIC-Click Membranes Using Hydrothiolation Reaction In this example, the flexibility of click chemistry is demonstrated as a click membrane functionalized with a hydrophobic ligand is demonstrated; a single polymerization step forms the membrane polymer network with a hydrophobic ligand (1-octane thiol) included in its network. By controlling the thiol/alkene ratio in the polymerization mixture, the residual alkene population can be varied, and, in principal, can be used in later steps to anchor additional molecules or ligands having the same or different chemical or physical properties.

In this membrane formulation class, 2,2'-(ethylenedioxy) diethanethiol (EDDET) monomer and both 1,4-dithioerythritol (DDT) and (+)-N,N'-diallyltartramide (DATA) co-monomers, were used as building monomers, while 1,3, 5-triallyl-1,3,5-triazine-2,4,6(1H,3H,5H)-trione (TATATO) and 1,7-octadiyne (OctDi) were used as crosslinkers. One-octane thiol was included in the formula to add a hydrophobic pendant or end group to the polymer. The solvent system included N,N'-dimethylacetamide (DMAc), sodium dodecyl sulfate (SDS), ethylene glycol (EG), tetra(ethylene glycol) (TetEG), and water, all in varying amounts. 4-(2-Hydroxyethoxy)phenyl-(2-hydroxy-2-propyl)ketone (IRGACURE 2959) was used as photoinitiator.

The reaction components (FIG. 19), except the dithiol (EDDET), were mixed in the solvent mixture until completely dissolved. Then, EDDET was added 10-15 min prior to casting. Membranes were cast and polymerized as described previously. Mass gain, wetting time, and initial flux of each membrane coupon (7.7 cm in diameter—using R.O. water) were determined.

Figures 19, 20:
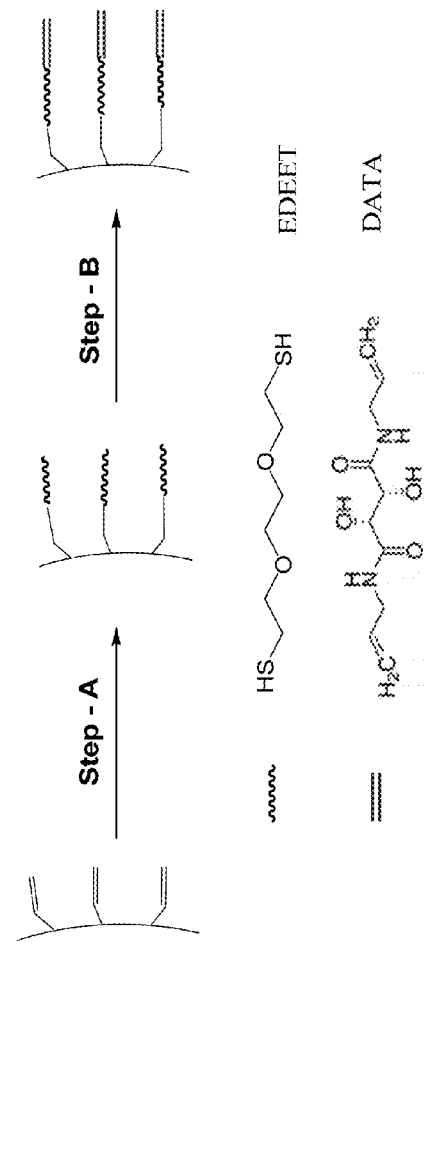
FIG. 19 tabulates the reaction components (wt. %) and solvents (wt. %) used in the preparation of HIC membranes formed by one-step polymerization and functionalization.
FIG. 20 depicts a schematic representation of a two-step graft extension process beginning with an alkene-functionalized membrane.

As shown in FIG. 19, it is possible to make membranes with variable permeability and IgG binding capacity through a single polymerization step that includes a hydrophobic ligand in the reaction mixture. See Table 10.

TABLE 10

Functionalized HIC-click membrane use in bio-separation

| Formula | Alkene/thiol ratio | RO water Flux (kg/m$^2$h) | HIC Mode IgG Binding Capacity$_{10BT\%}$ (mg/mL) |
|---|---|---|---|
| CLK-EN-411 | 1.237 | 4835 | 7.9 |
| CLK-EN-417 | 1.093 | 13635 | 8.4 |

Example 18—Post-Polymerization Step-Wise Grafting Process for Controlled or Extended Graft Architecture Via Hydrothiolation One major advantage of using hydrothiolation for gel functionalization is the ability to use the same reaction chemistry to introduce other monomers in later steps. Moreover, because of the specificity that characterizes click chemistry, it is possible to perform multi-step grafting processes, which can introduce pendant building blocks and functional groups in a very controlled manner.

To demonstrate this capability, selected membranes containing residual alkene functional groups were subject to stepwise grafting processes. The net result of this two-step grafting process is to build an arm extending out of the surface that has defined structure and length, as shown in FIG. 20.

In the first step, a dithiol monomer (EDDET) was used in excess to convert the gel surface functionality from alkene to thiol groups. Membrane coupons of 7.7-cm diameter were weighed then wetted with water, after which the coupons were transferred individually to plastic zip bags loaded with 4 mL of 10 wt % of dithiol (EDDET) in DMAc and 18 mg of photoinitiator (ACVA). Each reaction bag was stirred then exposed to UV light for 7 minutes, then the coupons were rinsed with 10 mL DMAc.

In the second step, an excess of di-alkene monomer (DATA) was reacted with the thiol-enriched membrane via a hydrothiolation grafting reaction to make a final membrane that contains alkene functional groups extended from the surface. Membrane coupons were transferred individually to new plastic zip bags loaded with 4 mL of 10 wt % of di-alkene monomer (DATA) in DMAc with ~18 mg of photoinitiator (ACVA). The reaction bags were exposed to UV light for another 7 minutes, then the membrane coupons were rinsed with DMAc, followed by several washes in water, then dried at room temperature. The final membrane weight was recorded.

Results, as shown below in Table 11, demonstrate that membrane mass gain increased slightly while permeability (measured by water flux) decreased significantly subsequent to the two step grafting reaction. Grafted membrane with permeabilities >1000 kg/m$^2$ h were used for subsequent Protein A ligand attachment to help probe for the successful incorporation of reactive alkene groups via this process and the effect on membrane protein binding capacity. Indeed, measurable IgG binding capacity indicates successful ligand grafting to the membrane surface (Table 11). Also, an increase in IgG binding capacity, post-grafting, is only seen for CLK-EN-224 where the mass gain was the greatest, suggesting the highest grafting yield.

This approach has a strong potential for modifying and optimizing the graft structure as it provides an efficient tool to construct a well-defined multi-unit grafts (or branches) that extend from the surface to modify the membrane surface properties, reactive group density, and/or permeability.

TABLE 11

Membrane performance after two-step grafting reaction

| Membrane | Alkene/thiol ratio | Mass gain wt. % | | IgG Binding Capacity$_{10\%B.T}$ (mg/mL) | | RO Flux (kg/m$^2$h) | |
|---|---|---|---|---|---|---|---|
| | | Initial | After Reaction | Initial | After Reaction | Initial | After Reaction |
| CLK-EN-224 | 1.129 | 238 | 251 | 6 | 11.1 | 17189 | 3996 |
| CLK-EN-287 | 1.135 | 267 | 270 | 10.2 | NA | 6972 | 170 |
| CLK-EN-291 | 1.159 | 264 | 266 | 9.8 | NA | 10172 | 250 |
| CLK-EN-301 | 1.211 | 243 | 249 | 9.6 | 8.7 | 13841 | 4151 |

Example 19—Double Polymerization Process for Constructing Covalently Connected "Two Phase" Membranes Another approach to exploit the capability of alkene-containing membranes to undergo click hydrothiolation reactions involves performing in situ hydrothiolation polymerization of monomers/crosslinkers that will form a second polymeric phase within the pores, and simultaneously covalently bond it to the underlying gel.

A membrane formula that has high permeability (CLK-EN-224) was selected to make four sheets of the base membrane (first phase) on a pre-weighed 7"×8" porous support substrate sheet (non-woven polypropylene mesh), as described above. Each sheet of the CLK-EN-224 membrane was individually placed on polyethylene sheet and impregnated with 12 g of polymerization solution described in FIG. 21—A/B/C/D. The impregnated membrane was subsequently covered with another polyethylene sheet and was pressed gently in a circular motion by hand in order to remove excess solution and any entrapped air bubbles. The polymerization process was initiated by irradiating with UV light (~350 nm) in a closed chamber for 10 min, then washed and dried as described above (General methods—Membrane preparation section).

The final weight and mass gain of each membrane were determined, then the increase of mass gain due to the grafted second phase polymerization was calculated for each formula. The double polymerization membranes were then grafted with mercaptosuccinic acid to introduce carboxylate groups to the membrane gel (see general methods section), which allow the membrane to function as a cation exchange media for protein bio-separation. In addition, the membranes were also grafted with protein A ligands, which enable the membrane to function as bio-affinity separation media (see general methods section for grafting and testing protocols).

Examining the resultant membranes (FIG. 22, CLK-EN-224 A/B/C/D) for their mass gain, permeability (flux), and binding capacity (in both cation exchange and bio-affinity modes) demonstrates that it is possible to construct a second phase polymeric gel within the first gel phase, and as a result, make a final composite with unique properties.

Mass gains of the "two-phase" membranes were higher than the base membrane, and the flux values were lower (FIG. 22). Binding capacities of the "two-phase" membranes were different than the base membranes. CEX IgG binding capacities appear to be inversely correlated to mass gain but directly correlated to water flux.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A composite material, comprising:
a support member, comprising a plurality of pores extending through the support member; and
a macroporous cross-linked gel, wherein the cross-linked gel comprises a polymer derived from a first monomer and a first cross-linker;
wherein
the macroporous cross-linked gel is located in the pores of the support member;
the macropores of the macroporous cross-linked gel are smaller than the pores of the support member;
the first monomer comprises two thiol functional groups; and the first cross-linker comprises (i) at least three carbon-carbon double bonds, (ii) at least two carbon-carbon triple bonds, or (iii) at least one carbon-carbon triple bond and at least one carbon-carbon double bond.

2. The composite material of claim 1, wherein the first monomer is 2,2'-(ethylenedioxy)diethanethiol (EDDET), 1,2-ethanedithiol, 1,4-butanedithiol, PEG dithiol, 1,6-hexanedithiol, 2,2'-thiodiethanethiol, ethane-1,2-diyl bis(3-mercaptopropanoate), hexa(ethylene glycol) dithiol, tetra(ethylene glycol) dithiol, 1,16-hexadecanedithiol, benzene-1,2-dithiol, benzene-1,3-dithiol, benzene-1,4-dithiol, biphenyl-4,4'-dithiol, p-terphenyl-4,4"-dithiol, (S)-2-aminobutane-1,4-dithiol hydrochloride, 4-phenyl-4H-(1,2,4)triazole-3,5-dithiol, 5-(4-chlorophenyl)-pyrimidine-4,6-dithiol, 1,4-benzenedimethanethiol, 2-mercaptoethyl ether, or L-(−)-dithiothreitol.

3. The composite material of claim 1, wherein the polymer is derived from the first monomer, the first cross-linker, and a second monomer, wherein the second monomer comprises two terminal carbon-carbon double bonds.

4. The composite material of claim 3, wherein the second monomer is tri(ethylene glycol) divinyl ether (TEGDV), 1,9-decadiene, 1,4-bis(vinyloxy)butane, diallylphthalate, diallyl diglycol carbonate, poly(ethylene glycol) divinyl ether, divinyl glycol, divinylbenzene, divinyl sulfone, 1,4-butanediol divinyl ether, allyl ether, allyl sulfide, 1,4-bis(4-vinylphenoxy)butane, 1,5-hexadiene, dipentene, (R)-(+)-limonene, (S)-(−)-limonene, N,N'-methylenebis(acrylamide), or N,N'-ethylenebis(acrylamide).

5. The composite material of claim 4, wherein the polymer is derived from the first monomer, the first cross-linker, the second monomer, and a third monomer, wherein the third monomer is (+)-N,N'-diallyltartramide (DATA), diallyl disulfide, diallyl carbonate, diallyl maleate, diallyl succinate, trimethylolpropane diallyl ether, 1,1-diallyl-1-docosanol, 1,1-diallyl-3-(1-naphthyl)urea, 1,1-diallyl-3-(2-ethylphenyl)urea, 1,2-diallyl-1,2-cyclohexanediol, 2,6-diallyl-metacresol, N,N-diallyl-2-hydroxypropanamide, 1,4-pentadien-3-ol, trimethyl(propargyl)silane, or propargylamine.

6. The composite material of claim 1, wherein the first cross-linker is 1,3,5-triallyl-1,3,5-triazine-2,4,6(1H,3H,5H)-trione (TATATO), 1,6-heptadiyne, 1,7-octadiyne, 1,8-nonadiyne, 1,9-decadiyne, propargyl acrylate, 4-arm PEG norbornene, trimethylolpropane triacrylate, tetra-alkyne poly(ethylene glycol), 2,4,6-triallyloxy-1,3,5-triazine, triallylamine, triallyl borate, triallylphosphine, diallyl fumarate, 3-(allyloxy)-1-propyne, glyoxal bis(diallyl acetal), tetraallylsilane, propargyl ether, or squalene.

7. The composite material of claim 1, wherein the cross-linked gel further comprises a plurality of grafted end-groups.

8. The composite material of claim 7, wherein the grafted end-groups are derived from a molecule having a thiol functional group or a molecule having an unsaturated carbon-carbon bond.

9. The composite material of claim 8, wherein the grafted end-groups are derived from a molecule having a thiol functional group; and the molecule having a thiol functional group is 3-mercaptopropionic acid, 1-mercaptosuccinic acid, a peptide having a cysteine residue, a protein having a cysteine residue, cysteamine, 1-thiohexitol, poly(ethylene glycol) 2-mercaptoethyl ether acetic acid, poly(ethylene glycol) methyl ether thiol, 1-thioglycerol, 2-naphthalenethiol, biphenyl-4-thiol, 3-amino-1,2,4-triazole-5-thiol, 5-(trifluoromethyl)pyridine-2-thiol, 1-[2-(dimethylamino)ethyl]-1H-tetrazole-5-thiol, 1-propanethiol, 1-butanethiol, 1-pentanethiol, 1-hexanethiol, 1-octanethiol, 8-amino-1-octanethiol hydrochloride, 3,3,4,4,5,5,6,6,7,7,8,8,8-tridecafluoro-1-octanethiol, 8-mercapto-1-octanol, or γ-Glu-Cys.

10. The composite material of claim 7, further comprising a first ligand, wherein the first ligand comprises:
   an ion exchange functionality, a hydrophobic interaction moiety, or a biomolecule; and
   at least one grafting group.

11. The composite material of claim 10, wherein the grafting group is an unsaturated carbon-carbon bond.

12. The composite material of claim 10, wherein the grafting group is a thiol functional group.

13. The composite material of claim 10, wherein the first ligand is a biomolecule comprising at least one thiol functional group.

14. The composite material of claim 13, wherein the biomolecule is a protein A derivative.

15. The composite material of claim 10, further comprising a second ligand, wherein:
   the polymer is derived from the first monomer, the first cross-linker, and a second monomer;
   the first ligand is a biomolecule comprising a least three thiol functional groups;
   the second monomer comprises two terminal carbon-carbon double bonds;
   the second ligand is a biomolecule comprising at least three thiol functional groups; and
   the second ligand is a second cross-linker.

16. The composite material of claim 15, wherein the second ligand is a protein A derivative.

17. The composite material of claim 15, wherein the second monomer is poly(ethylene glycol) divinyl ether.

18. The composite material of claim 15, further comprising a third ligand, wherein:
   the polymer is derived from the first monomer, the first cross-linker, the second monomer, and a third monomer;
   the third monomer comprises two terminal carbon-carbon double bonds;
   the third ligand is a biomolecule comprising at least three thiol functional groups; and
   the third ligand is a third cross-linker.

19. The composite material of claim 18, wherein the third ligand is a protein A derivative.

20. The composite material of claim 18, wherein the third monomer is poly(ethylene glycol) divinyl ether.

21. The composite material of claim 1, wherein the composite material is a membrane.

22. A method, comprising the step of:
   contacting at a first flow rate a first fluid comprising a substance with a composite material of claim 1, thereby adsorbing or absorbing a portion of the substance onto the composite material.

* * * * *